United States Patent [19]

Halpern et al.

[11] Patent Number: 5,431,901
[45] Date of Patent: Jul. 11, 1995

[54] SELECTIVE ISOTOPIC LABELING OF SPIN LABELS FOR ELECTRON SPIN RESONANCE SPECTROSCOPY

[76] Inventors: Howard J. Halpern, 5336 S. University Ave. #2, Chicago, Ill. 60615; Beverly A. Teicher, 135 Hunting Rd., Needham, Mass. 02192

[21] Appl. No.: 227,793

[22] Filed: Aug. 3, 1988

[51] Int. Cl.⁶ .................. C07D 207/46; C07D 211/94
[52] U.S. Cl. .................. 424/9.33; 436/173; 546/216; 546/223; 548/215; 548/531; 548/537; 548/539; 548/540; 548/542; 564/297
[58] Field of Search ............ 564/297, 298, 299; 548/215, 542, 537, 539, 540, 531; 546/242, 244, 184; 514/374, 423, 424, 425; 424/9; 436/173

[56] References Cited

U.S. PATENT DOCUMENTS

| | | | |
|---|---|---|---|
| 4,665,185 | 5/1987 | Winter et al. | 548/542 X |
| 4,677,049 | 6/1987 | Griffing et al. | 564/299 X |
| 5,036,014 | 7/1991 | Eisohly et al. | 436/173 X |
| 5,104,641 | 4/1992 | Rosen | 424/9 |
| 5,256,397 | 10/1993 | Rosen | 436/173 X |

OTHER PUBLICATIONS

Halpern, et al.; Journal of Magnetic Resonance, Series A 103, pp. 13–22, (1993).
Halpern, et al.; Journal of Magnetic Resonance, 90, pp. 40–51, (1990).
Bales, et al.; Journal of Magnetic Resonance, 98, pp. 299–307, (1992).
Bowman, et al.; Pure and Applied Chemistry, 62, No. 2, pp. 271–274 (1990).
Hyde, et al.; Journal of Magnetic Resonance, 56, pp. 125–130 (1984).
Morrison and Boyd; Organic Chemistry, 2nd ed. (1966), pp. 354–355.
Liberles, Introduction to Theoretical Organic Chemistry, (1968), p. 34.

*Primary Examiner*—Joseph Paul Brust
*Attorney, Agent, or Firm*—Marshall, O'Toole, Gerstein, Murray & Borun

[57] ABSTRACT

Selective isotopic-labeling of spin label compounds, used in electron spin resonance spectroscopy to detect, measure and monitor the presence of paramagnetic species, increases the sensitivity of the electron spin resonance technique in assays for paramagnetic species, such as the determination of oxygen tension in solution or in a biological sample, like a living organism. Spin label compounds, such as nitroxides, like 3-carbamoyl-2,2,5,5-tetramethyl-3-pyrroline-1-yloxyl (CTPO), are selectively, but not completely, isotopically-labeled, such as partially deuterated, to increase the sensitivity and reliability of assays employing electron spin resonance spectroscopic measurements.

10 Claims, 8 Drawing Sheets

1G

1G

FIG. 6
Low O₂   Higher O₂
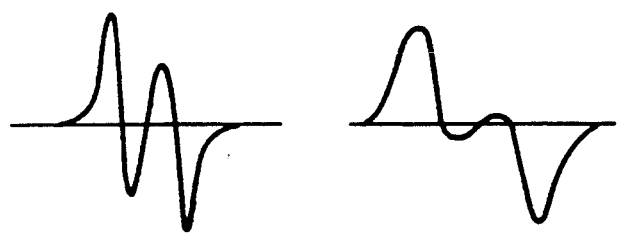
FIG. 7

SELECTIVE ISOTOPIC LABELING OF SPIN LABELS FOR ELECTRON SPIN RESONANCE SPECTROSCOPY

FIELD OF THE INVENTION

The present invention relates to a class of compounds and to a method of assaying a test sample for the presence and concentration of a paramagnetic species. More particularly, the present invention relates to an improved method of assaying a test sample, such as a solution or a biological sample, like a living organism, for the presence and concentration of a paramagnetic species through electron spin resonance spectroscopic techniques. The improved method of the present invention utilizes a new class of compounds as the spin label in an electron spin resonance technique to detect, measure and monitor the paramagnetic species present in the test sample. The new spin label compounds of the present invention include nitroxides, like 3-carbamoyl-2,2,5,5-tetramethyl-3-pyrroline-1-yloxyl (CTPO), that have been selectively isotopically-labeled such that at least one, but not all, of the non-labile hydrogen atoms of spin label have been replaced by deuterium atoms. An especially useful selectively isotopically-labeled spin label is 4-H-perdeuterated CTPO, a nitroxide that increases the sensitivity of electron spin resonance techniques to allow the accurate and reliable determination of a paramagnetic species, such as molecular oxygen, in a test sample, such as a solution or a living organism.

BACKGROUND OF THE INVENTION AND PRIOR ART

Electron spin resonance spectroscopy (ESR) is among the most useful methods of detecting, measuring and studying paramagnetic species. The ESR spectrum is an absorption spectrum showing the energy required to change the spin state of an unpaired electron from a preferred alignment with an externally applied magnetic field to the less stable spin state alignment against the externally applied magnetic field. Similar to nuclear magnetic resonance spectra, the ESR spectra show signal splitting because of coupling of the spins of nearby nuclei with atoms that carry the unpaired electron.

ESR has been used spectroscopically to determine the presence and concentration of paramagnetic species in a test sample under analysis. Typically a very small test sample is subjected to a fixed radio frequency field in the so-called X band (e.g., 9.5 Gigahertz) and to a time-varying homogenous magnetic field. The resulting absorption spectrum is detected as a signal of the presence and concentration of a paramagnetic species within the test sample having electron spin resonances corresponding to magnetic field intensities that fall within the detected spectrum for the particular fixed radio frequency being used. Typically the magnetic field is on the order of several thousand gauss and is provided by placing the sample between the poles of an electromagnet. The time variation in the magnetic field is accomplished by varying the current in a pair of sweep coils positioned respectively between each pole of the electromagnet and the sample.

As a result, ESR spectroscopy can be used to detect paramagnetic species, like free radicals; to measure the concentration of paramagnetic species; and to provide information as to the structure of the paramagnetic species. Furthermore, ESR spectroscopic techniques are extremely sensitive, such that, under favorable conditions, a free radical concentration of as low as $10^{-12}M$ can be detected. Therefore, ESR spectroscopic techniques have been used to study free radical intermediates in organic reactions, to study the generation and decay of free radical species in oxidations catalyzed by enzymes, to detect drug metabolites, to detect quinones that are present in all biological species, to study the mechanism of drug or toxin interactions with cellular constituents, and to study the fixing of carbon dioxide in algae during photosynthesis.

However, not all paramagnetic species are amenable to direct detection and measurement by ESR spectroscopic techniques. For example, molecular oxygen is a stable free radical having two unpaired electrons. However, the direct measurement of the concentration of molecular oxygen, especially in aqueous solution, by ESR spectroscopic techniques is not possible because the ESR absorption signal is too broad. The extreme breadth of the ESR absorption signal for molecular oxygen is due to the existence of two intramolecular spins and four intramolecular spin states that have extremely short-lived spin states, and that are in an environment of frequent molecular collisions. Since the breadth of the spectral signal, $\Gamma$, is equal to the inverse of the average lifetime of the spin $(T_1)$, the very small $T_1$ for molecular oxygen, especially in aqueous solution, makes the breadth of the spectral signal immeasurably large.

Molecular oxygen, however, can be detected and measured, even in aqueous solution, through an ESR spectroscopic technique that determines the effect of molecular oxygen on the lifetimes of the longer-lived spin states of other paramagnetic compounds. The longer-lived spin states are found in paramagnetic organic molecules having a stable unpaired electron. Such paramagnetic organic molecules are observable by ESR spectroscopy and commonly have narrow, well-measured hyperfine spectra that are detectably broadened in the presence of molecular oxygen. The broadening of the hyperfine spectra is essentially directly proportional to the molecular oxygen concentration in the test sample, and therefore the degree of spectrum broadening is used to quantify the amount of molecular oxygen in the test sample.

The broadening of the ESR spectrum occurs because of an interaction between the spin of the free electron present on the paramagnetic organic molecule and the spins of the unpaired electrons of the molecular oxygen. The exchange of spins between the paramagnetic organic molecule and the molecular oxygen allows the relatively long-lived spin state of the paramagnetic organic molecule to couple with the extremely short-lived spin states of molecular oxygen, thereby short-circuiting the normal spin relaxation mechanisms of molecular oxygen. The resulting shortened lifetime of the spin state of the paramagnetic organic molecule is reflected in a broadening of the narrow spectral line of the paramagnetic organic molecule. In this ESR spectroscopic technique, the amount of the paramagnetic organic molecule added to the test sample need only be high enough to generate a detectable ESR spectrum and to permit measurement of oxygen-induced spectrum broadening. Accordingly, the sharpest, narrowest ESR spectra correspond to the lowest molecular oxygen concentrations.

The paramagnetic organic molecules having an unpaired electron and used to help detect, measure and monitor the concentration of molecular oxygen, organic-free radicals and other paramagnetic species in a test sample are termed spin labels. Therefore, in order to determine the oxygen concentration, or oxygen tension, of a test sample by ESR spectroscopic techniques, a spin label is added to the test sample to act as a reporter substance. Consequently, a suitable spin label should be capable of incorporation into the test sample and capable of reporting information concerning the paramagnetic species of interest to a detector, such as an ESR spectrometer; should have paramagnetic properties different from the paramagnetic properties of the paramagnetic species of interest in the test sample; and should not interact with the test sample, physically or chemically, to cause measurable changes in the test sample.

The most advantageous spin labels are stable paramagnetic organic molecules having a free unpaired electron and of low reactivity. Although a variety of inorganic spin labels have been employed, such as nitric oxide, paramagnetic transition metal ions and lanthanide ions, the most useful spin labels, both in solution and in biological samples, including living organisms, have been organic spin labels, especially the protected nitroxide compounds of general structural formula (I) that include the paramagnetic nitroxyl moiety.

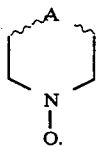

The nitroxides of general structural formula I have been widely used as spin labels because they are extremely stable, and extremely inert, due to the protective effect of the four methyl groups substituted on the alpha and alpha' carbon atoms. The stability of the free radical portion of the molecule of general structure I, i.e., the nitroxyl moiety, allows a variety of chemical reactions to be performed on the A portion of the molecule in order to alter the physical and chemical characteristics of the nitroxide spin label molecule without destroying the free radical portion of the molecule. Similarly, the stability of the free radical nitroxyl portion of the nitroxide allows the nitroxyl moiety to remain unchanged in biological samples, therefore allowing the study of free radical and paramagnetic species both in vitro and in vivo. It also should be noted that the four methyl groups substituted on the alpha and alpha' carbon atoms help stabilize the nitroxide molecule by making a disproportionation reaction between two nitroxide molecules to yield a nitrone and a hydroxyamine, and therefore destroy the paramagnetism of the molecule, more difficult.

The nitroxides of structural formula I have proven very useful in ESR spectroscopic techniques to measure molecular oxygen tension, or molecular oxygen concentration, in aqueous solution. For example, it is well known that the interaction of dissolved oxygen molecules and nitroxide free radicals, through Heisenberg spin-exchange, causes broadening of the ESR spectral lines. Therefore, with a suitable nitroxide spin label, this property can be used to quantitate oxygen concentrations in solution. In addition, the nitroxides do not consume oxygen, thereby allowing the detection and measurement of slow-rate oxygen consumption processes over a long period of time. Consequently, the nitroxide spin label CTPO has been used to monitor the concentration of dissolved oxygen in the aqueous regions of biological samples.

The effect of molecular oxygen on the width of an ESR spectra of a nitroxide spin label was originally reported by G. F. Pake and T. R. Tuttle, Jr. in the publication, nomalous Loss of Resolution of "A Paramagnetic Resonance Hyperfine Structure in Liquids", *Physical Review Letters*, 3(9):423 (1959), wherein the authors theorized that the spectrum widening effect due to molecular oxygen was an anomaly. However, it was this initially-theorized anomaly that eventually led to the $T_2$-based, or spectrum width, spin label oxymetry method of determining the molecular oxygen concentration of a test sample. M. J. Popovitch, in the publication "Electron Spin Resonance Oxygen Broadening", *J. Phys. Chem.* 79 (11): 1106–1109 (1975) and J. M. Backer, J. M. Budker, S. L. Eremenko, and Yu N. Molin, in the publication "Detection of the Kinetics of Biochemical Reactions with Oxygen Using Exchange Broadening in the ESR Spectra of Nitroxide Radicals", *Biochemica et Biophysica Acta* 460:152–156 (1977) used the spectra broadening effect of molecular oxygen on the ESR spectrum of a nitroxide spin label in a biological sample to make indirect measurements of the ambient oxygen tension. Popovitch and Backer each utilized nitroxide compounds as the spin labels, particularly nitroxide nitrogen-heterocycles having di-methyl substitutions on the alpha and the alpha' carbon atoms, as depicted in structural formula I. These small nitroxide spin label molecules rotated sufficiently rapidly in solution, and in the hydration shells of a biological environment, to average out hyperfine and coupling pseudotensor anisotropies, therefore yielding, in the absence of oxygen, narrow, well-defined hydrogen hyperfine spectra. However, with the addition of oxygen to the test sample, these narrow hydrogen hyperfine splittings, in a roughly proportionate fashion, broaden and disappear. Oxymetry, or oxygen measurements, performed by this ESR method utilize the broadening effect of oxygen concentration on the linewidth of the proton hyperfine lines of the ESR spectra and, therefore, are termed $T_2$-based.

However, the use of a nitroxide spin label in an ESR method to measure the oxygen tension of a test sample still possesses several disadvantages. To date, two approaches have been used for $T_2$-based ESR spin label oxymetry, each having advantages and disadvantages. The first approach is the standard nitroxide spin label ESR oxymetry method as described by Lai, et al., in the publication "ESR Studies of $O_2$ Uptake By Chinese Hamster Ovary Cells during the Cell Cycle" *Proc.Natl. .Acad. Sci. USA* 79:1166–1170 (1982) and by the previously cited publication of Backer et al. The ESR spectrum of an aqueous solution of the nitroxide spin label 3-carbamoyl-2,2,5,5-tetramethyl-3-pyrroline-1-yloxyl (CTPO) shows a broadening of the proton hyperfine lines upon the addition of oxygen, such that the height of the hyperfine lines relative to the nitrogen triplet is reduced roughly proportionately to the oxygen tension. In this technique, a ratio between the height of a proton hyperfine line and the overall height of the spectrum of the nitrogen line under consideration is found, and the oxygen tension determined. In this standard oxymetry method, the ratio used to determine oxygen tension is independent of the amount of nitroxide spin label present in the test sample, except for normal signal-to-noise limitations. According to this standard method, the ESR data pertaining to the measurement of the oxygen tension is related to the spectral shape and is independent of the spectral height.

The above-described standard method suffers a serious disadvantage because the very narrow hyperfine lines, as a principal source of the width of the nitroxide signal, are dispersed over the full width of the nitroxide signal. Furthermore, these hyperfine lines are resolved only by reduction of the ESR spectrometer field modulation amplitude, thereby reducing the intensity of the spectral signal. As a result, only a relatively small fraction of the nitroxide spin label is contributing to the signal at any one field point therefore yielding relatively low signal intensity.

A second ESR oxymetry method that has been investigated uses a perdeuterated nitroxide spin label. The hyperfine coupling of the deuterium to the unpaired electron of the nitroxide is roughly one-seventh the hyperfine coupling of hydrogen. Therefore, the deuterium hyperfine lines are so closely spaced that the hyperfine lines are barely resolvable by ESR spectrometers. Therefore, the resulting ESR spectrum is a narrow, easily measured single line. In contrast to the ESR spectrum of the standard, hydrogenated nitroxide spin label described above, measurements from ESR spectra of the perdeuterated nitroxide spin label are easier to perform because all of the perdeuterated nitroxide spin label is contributing to the signal over a very narrow region. Furthermore, it has been shown that the width of this single line signal is very sensitive to, and is roughly proportional to, the ambient oxygen tension. As a result, the height of the narrow ESR spectrum of a deuterated nitroxide spin label varies dramatically with the oxygen tension because at a fixed, small modulation field amplitude the height of a line described by the first derivative of a Lorentzian shape is proportional to the inverse square of the width of the line.

However, the perdeuterated nitroxide spin labels also present disadvantages when used in ESR oxymetry methods. For example, unlike the hydrogenated nitroxide spin labels, the height of the perdeuterated nitroxide spin label spectrum is sensitive both to the oxygen tension of the test sample and to the concentration of spin label in the test sample. In addition, the dependence of the perdeuterated spin label signal height upon perdeuterated spin label concentration, at constant oxygen tension, is not linear over the entire range of spin label concentration. The linear increase in signal height with increasing concentration of perdeuterated spin label, at low concentrations of perdeuterated spin label, is eventually overcome by the self-broadening effect of the perdeuterated spin label at higher concentrations of perdeuterated spin label, therefore yielding a linear decrease of the signal height at higher perdeuterated spin label concentrations.

If a test sample has a uniform perdeuterated spin label distribution, data relating to the amount of perdeuterated spin label contributing to the ESR spectrum can be determined from the double integral of the derivative ESR spectrum. However, the sensitivity of the oxygen tension measurement will be reduced by the uncertainties inherent in that calculation. In addition, in a sample having a heterogeneous distribution of the perdeuterated spin label, such as in biological samples, the contribution of the spin label concentration to the spectrum is even more difficult to determine, as is the interpretation of the spin label concentration-weighted spectral width. Therefore, given the sensitivity of the spectral width to perdeuterated spin label concentration, and the difficulty of reliably determining the contribution of perdeuterated spin label concentrations from heterogeneous samples, a reliable and accurate quantitative measurement of oxygen tension from actively metabolizing heterogeneous tissue is difficult. Furthermore, perdeuterated nitroxide spin labels may contain labile, or exchangeable, hydrogen/denterium atoms on functional groups at sites that effect the spectral linewidth. Therefore, in a method to determine the oxygen tension in live organisms, the deuterium present at these labile sites would be exchanged for hydrogen, and thereby render the oxygen tension measurement unreliable.

Accordingly, to date, the compounds used as spin labels in ESR studies of paramagnetic species have suffered from sacrificing one beneficial property in order to achieve another beneficial property. Prior to the present invention, no known class of compounds has effectively provided a strong, narrow signal that is essentially independent of nitroxide spin label concentration in the test sample. Therefore, it would be advantageous to have a spin label for use in an ESR-based assay method, such as oxymetry, that provides a strong, narrow spectral line that eliminates much of the usual signal-to-noise problem, as demonstrated by the perdeuterated nitroxide spin labels, and also provides an ESR spectrum that is essentially independent of the amount of nitroxide spin label present in the test sample, as demonstrated by the standard, hydrogenated nitroxide spin labels. Surprisingly and unexpectedly, the new class of compounds of the present invention, the selectively isotopically-labeled spin labels, provides the advantages, and avoids the disadvantages, of both the standard hydrogenated nitroxide spin labels and the perdeuterated nitroxide spin labels.

Therefore, in accordance with the present invention, a new class of compounds is used in an improved method of assaying a test sample, such as a solution or a living organism, for the presence and concentration of a paramagnetic species, such as molecular oxygen, through ESR spectroscopic techniques. The new class of spin label compounds include selectively isotopically-labeled nitroxide spin labels, wherein at least one, but less than all, of the non-labile hydrogen atoms have been replaced by deuterium atoms, or wherein an isotope of a particular atom replaces at least one, but not all, of the particular atoms present in the molecule. In addition, the new class of compounds sufficiently enhance the sensitivity of ESR spectroscopic techniques, such that low frequency ESR spectrometers, that yield weak signals, can be used in assays to detect, measure and monitor paramagnetic species in a test sample.

SUMMARY OF THE INVENTION

In brief, the present invention relates to a method of assaying a test sample for the presence and concentration of a paramagnetic species through electron spin resonance spectroscopy (ESR) techniques by utilizing a new class of spin label compounds. More particularly, the present invention relates to a method of assaying a test sample, such as a solution or a living organism, for the presence and concentration of a paramagnetic species, such as organic free radicals or molecular oxygen, by ESR spectroscopic techniques using selectively isotopically-labeled nitroxides as the spin label. Surprisingly and unexpectedly, the selectively isotopically-labeled nitroxides of the present invention increase the sensitivity of the ESR technique by providing a sharp, narrow ESR spectrum that is broadened, essentially proportionally, by the amount of the paramagnetic species present in the test sample; that is more measurably and correctably affected by the concentration of the spin label added to the test sample; and that allows the reliable and accurate detection, measurement and monitoring of a paramagnetic species in a test sample using a low frequency ESR spectrometer, such as a spectrometer capable of operating at frequencies less than 1 GHz, like from about 80 to about 300 MHz (megahertz).

The selectively isotopically-labeled spin label compound of the present invention can be any nitroxide compound that contains more than one non-labile atom of a particular chemical identity, wherein at least one, but not all, of the non-labile atoms of that particular identity have been replaced by an isotope of that atom. For example, a nitroxide spin label that contains the number, (n), non-labile nitrogen-14 atoms can have at least one, and up to (n-1), of the non-labile nitrogen-14 atoms replaced by the nitrogen-15 isotope in order to provide a selectively isotopically-labeled spin label of the present invention. A particularly effective selectively isotopically-labeled spin label of the present invention is the nitroxide, 3-carbamoyl-2,2,5,5-tetramethyl-3-pyrroline-1-yloxyl (CTPO), that has been selectively isotopically-labeled such that at least one, but not all, of the non-labile hydrogen atoms of the nitroxide CTPO have been replaced by deuterium atoms.

Therefore, it is an object of the present invention to provide a method of assaying a test sample for the presence and concentration of a paramagnetic species.

It is also an object of the present invention to provide a method of assaying a test sample, such as a solution or a biological sample, like a living organism, for the presence and concentration of a paramagnetic species by ESR spectroscopic techniques.

Another object of the present invention is to provide an ESR method of assaying a biological sample, like a living organism, either in vivo or in vitro, for the presence and concentration of a paramagnetic species, such as molecular oxygen or a drug metabolite.

Another object of the present invention is to provide an ESR method of assaying a test sample for a paramagnetic species, wherein the ESR method utilizes a new nitroxide spin label to enhance the sensitivity of the ESR technique.

Another object of the present invention is to provide a new nitroxide spin label for use in an ESR method to detect, measure and monitor the concentration of a paramagnetic species in a test sample, wherein the new nitroxide spin label increases the sensitivity of the ESR technique by providing a sharp, narrow ESR spectrum that responds essentially proportionally to the amount of paramagnetic species present in the test sample, and that is measurably and correctably affected by the amount of nitroxide spin label added to the test sample.

Another object of the present invention is to provide a nitroxide spin label for use in an ESR method to detect, measure and monitor the concentration of a paramagnetic species in a test sample such that the presence and concentration of the paramagnetic species in the test sample can be reliably and accurately determined by using a low frequency ESR spectrometer that operates below 1 GHz, such as in the range of from about 80 to about 300 MHz.

Yet another object of the present invention is to provide a nitroxide spin label to detect, measure and monitor the concentration of a paramagnetic species by ESR techniques, wherein the nitroxide spin label is selectively isotopically-labeled.

Another object of the present invention is to provide a selectively isotopically-labeled nitroxide that contains more than one non-labile atom of a particular chemical identity, and wherein at least one, but not all, of the non-labile atoms of that particular chemical identity have been replaced by an isotope of that atom.

Another object of the present invention is to provide a nitroxide spin label containing the number, (p), non-labile hydrogen atoms that have been selectively replaced with from one to (p-1) hydrogen isotopes, i.e., deuterium atoms, Still another object of the present invention is to provide a selectively isotopically-labeled nitroxide spin label to increase the sensitivity of an ESR method to determine the presence and concentration of a paramagnetic species, like molecular oxygen, in a test sample having the formula:

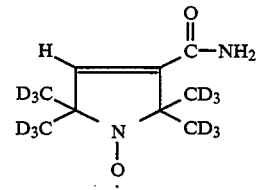

BRIEF DESCRIPTION OF THE DRAWINGS

The above and other objects and advantages and novel features of the present invention will become apparent from the following detailed description of the preferred embodiments of the invention illustrated in the accompanying figures illustrating the enhanced sensitivity of an ESR spectroscopic method to detect and measure the amount of a paramagnetic species in a test sample achieved by using the method and class of compounds of the present invention, wherein:

FIG. 6 is an absorption ESR spectrum of an aqueous solution of the selectively isotopically-labeled nitroxide, 4-H-perdeuterated CTPO, showing that increasing the oxygen tension of the solution reduces the valley, or dip, between the two absorbence peaks;

FIG. 7 is a derivative ESR spectrum, corresponding to the absorption ESR spectra of FIG. 5, showing the effect of increasing oxygen tension on the derivative ESR spectrum signal height and signal width, and defining the parameter r;

FIG. 8 is a series of derivative ESR spectra showing the effect of increased oxygen tension on the derivative ESR spectra of a solution of the nitroxide spin label 4-H-perdeuterated CTPO, and showing the reduction in the parameter r with increasing oxygen tension.

DETAILED DESCRIPTION OF THE PREFERRED EMBODIMENT

A new class of compounds, selectively isotopically-labeled nitroxide spin labels, are used in an electron spin resonance (ESR) spectroscopic method to measure, detect and monitor paramagnetic species, such as organic free radicals or molecular oxygen, in a test sample, such as a solution or a biological sample, like a living organism. As previously described, the direct measurement of certain paramagnetic species, such as molecular oxygen, by ESR spectroscopic techniques is not possible because the short-lived spin statues make the ESR spectrum immeasurably broad. Therefore, a reporter compound having a longer-lived spin state, i.e., a spin label, such as a nitroxide, is used to indirectly detect, measure and monitor the concentration of the paramagnetic species by ESR spectroscopic techniques by interacting with the short-lived spin state of the molecular oxygen. The overall result is a line broadening of the ESR spectrum of the nitroxide spin label that is essentially proportional to the molecular oxygen concentration of test sample.

Figure 1:
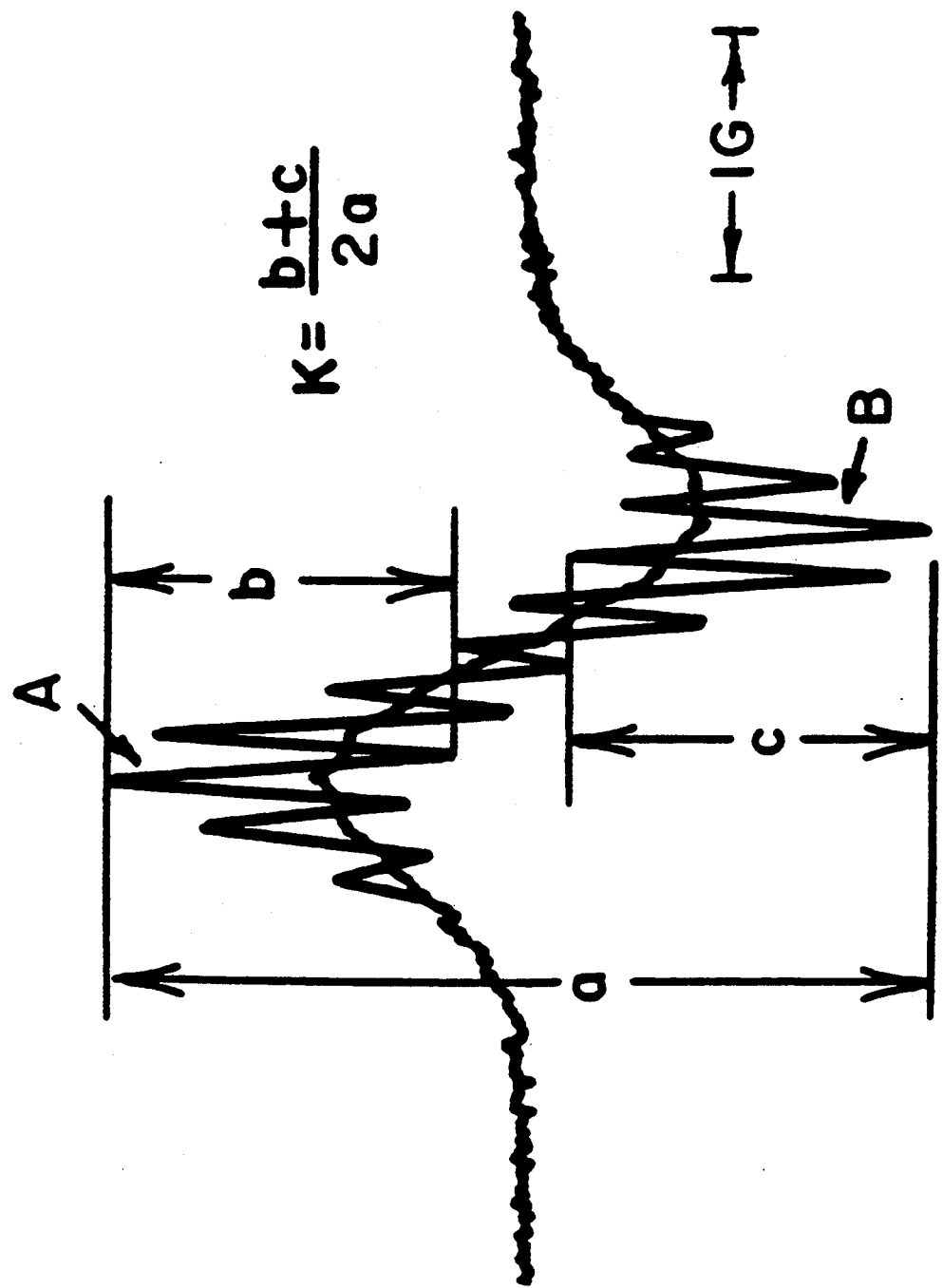
FIG. 1 is a high-frequency derivative ESR spectrum of the nitroxide CTPO showing the effect of molecular oxygen on the proton hyperfine lines of the spectrum and defining the parameter, K.

The effect of molecular oxygen on the ESR spectrum of the nitroxide spin label, 3-carbamoyl-2,2,5,5-tetramethyl-3-pyrroline-1-yloxyl (CTPO), is shown in FIG. 1. FIG. 1 is the derivative ESR spectrum of an aqueous solution that is 0.114 mM (millimolar) in CTPO, shown as structural formula II. It should be noted that in most ESR spectroscopic techniques, the pure absorption ESR spectrum is not plotted. The usual plot is the first derivative of the curve of absorption vs. magnetic field in order to provide a better signal-to-noise ratio. Therefore, when using high frequency ESR techniques, such as from about 1 to about 10 GHz (gigahertz, 1 GHz= $10^9$ cps), a well-oxygenated CTPO solution gives a simple biphasic ESR spectrum. However, upon purging the aqueous CTPO solution of oxygen, the derivative ESR spectrum is a well-defined ESR spectrum having relatively sharp proton hyperfine lines superimposed on the central line of the nitrogen triplet. As demonstrated in FIG. 1, the sharpening of the spectral lines in the absence of oxygen has allowed resolution of the hyperfine lines; and therefore such a well-resolved hyperfine spectrum of CTPO is an indication of hypoxia, or lack of oxygen, within the test sample. Such assay information is extremely important in the assay of living organisms.

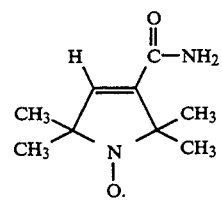

II

Figure 2:
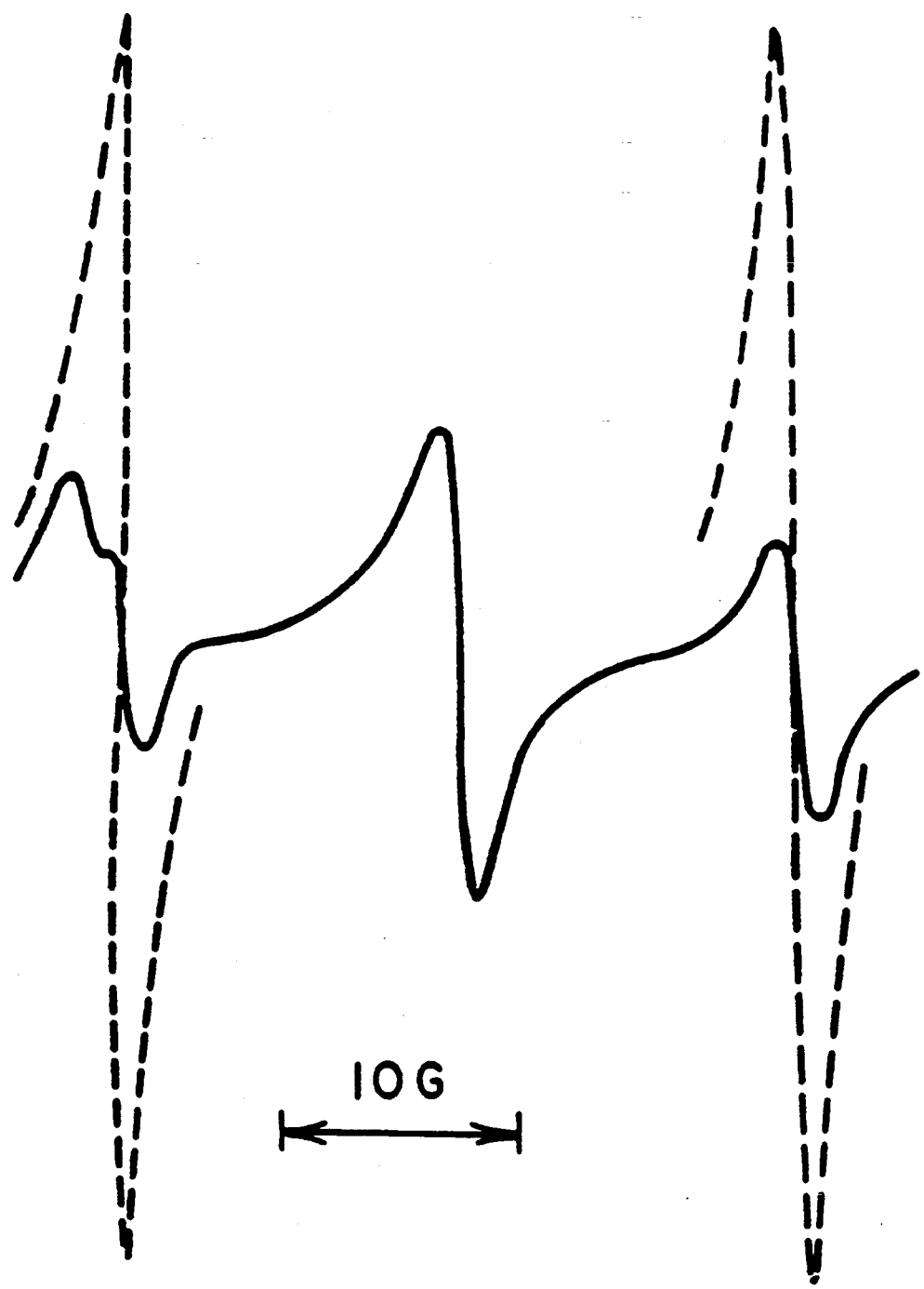
FIG. 2 is a low-frequency derivative ESR spectrum of the nitroxide CTPO showing the effect of oxygen tension in a live mouse on the ESR spectrum of the nitroxide spin label.

Oxygen tension, or oxygen concentration, measurements have been performed on live animals in an attempt to find a hypoxic condition. For example, FIG. 2 is a derivative ESR spectrum of the nitroxide spin label CTPO after injecting about 3 to 4 ml of saturated CTPO in phosphate buffer into the mouse. FIG. 2 shows a sharpening of the derivative ESR spectrum at a lower oxygen tension as demonstrated by the increase in the signal amplitude (dotted spectrum). Increasing the oxygen tension correspondingly produced a signal height decrease (solid spectrum).

As discussed above, the principal advantage of using the nitroxide CTPO as the spin label for ESR spectroscopic measurements of oxygen tension is that the measurement is independent of the amount of CTPO spin label present in the test sample, except for normal signal-to-noise considerations. It has been found that the oxygen tension of the test sample is roughly inversely proportional to the inverse of the ratio of the height of the proton hyperfine lines to the overall height of the spectral variation. This relationship is shown mathematically in Equation 1 -

$$K = \frac{b+c}{2a} ; \qquad \text{(Eq. 1)}$$

wherein the variables a, b and c that contribute to the parameter K are shown in FIG. 1, wherein the variables b and c Deflect the height of the proton hyperfine lines and the variable a reflects the overall height of the ESR spectrum. In general, the parameter K is an empirical measure of the hyperfine line contribution to the derivative ESR spectrum. As will be discussed more fully hereinafter, a graph of the empirical parameter r, that is defined similarly to the parameter K, vs. oxygen tension provides a roughly linear graph, such that after determining the r, or K, parameter for a test sample, the oxygen tension of the test sample can be found from a graph of oxygen tension vs. either r or K, depending upon the particular spin label compound used.

However, an ESR spectroscopic technique utilizing CTPO suffers from the disadvantage that the narrow proton hyperfine lines are dispersed over the full width of the nitroxide line. Therefore, the proton hyperfine lines are resolved only by reducing the ESR spectrometer field modulation amplitude. As a result, only a small fraction of the CTPO spin label is contributing to the signal at any one signal point, thereby producing a signal of relatively low signal intensity.

As also discussed above, by utilizing a perdeuterated nitroxide spin label, wherein all the hydrogen atoms of the nitroxide have been replaced by deuterium atoms, the above-mentioned disadvantage of a wide spectrum is overcome because the deuterium hyperfine coupling to the unpaired electron is roughly one-seventh that of the hydrogen hyperfine coupling. The overall result is deuterium hyperfine lines that are barely resolvable by ESR spectroscopic techniques, to therefore yield a sharp, strong, single line spectrum that is more easily resolved than the multipeaked hyperfine spectrum of CTPO shown in FIG. 1. For example, FIG. 3 shows the derivative ESR spectra of the nitroxide spin label, perdeuterated 2,2,6,6-tetramethyl-piperidin-4-oxy-1-yloxy, also known as perdeuterated TEMPONE, and illustrated as structural formula III:

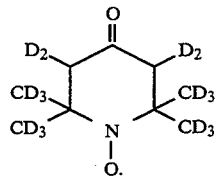

III

Figures 3A, 3B:
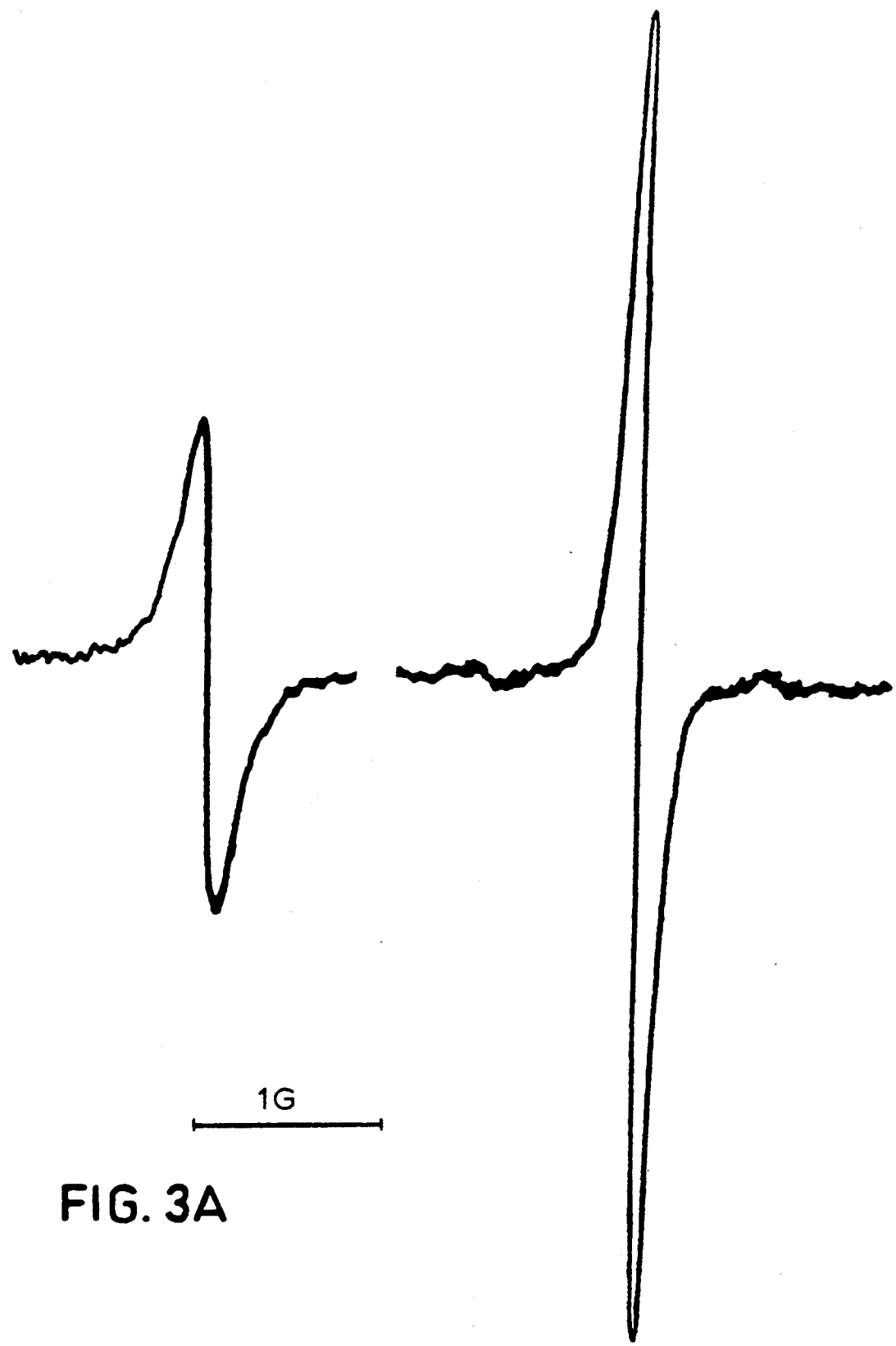
FIG. 3 is a derivative ESR spectrum of the nitroxide spin label perdeuterated TEMPONE, showing the effect of molecular oxygen concentration on the ESR signal width and ESR signal height.

In FIG. 3, the derivative ESR spectrum labeled A is an ESR spectrum of a solution of $2 \times 10^{-4}$M perdeuterated TEMPONE in deuterium oxide that has been equilibrated with air; spectrum B is an ESR spectrum of a solution of $2 \times 10^{-4}$M perdeuterated TEMPONE in deuterium oxide that has been made by hypoxic, or oxygen deficient. The dramatic difference in peak height between the derivative ESR spectra A and B of FIG. 3 is because all of the perdeuterated spin label compound is contributing to the signal intensity in a very narrow region (to give the strong, sharp single line spectrum of B), and because the width of the ESR spectrum of a perdeuterated spin label is very sensitive to, and proportional to, the concentration of a paramagnetic species, such as ambient oxygen tension, in solution. In turn, the height of the spectral signal varies dramatically with a change in spectral width because the height of the signal is inversely proportional to the square of the width of the signal for constant modulation field. Therefore, a small change in spectral width produces a large change in spectral height.

Figure 4A:
FIG. 4 is a derivative ESR spectrum, taken with a low frequency ESR spectrometer of an aqueous solution of the nitroxide CTPO shoeing the effect of molecular oxygen concentration on the ESR signal width and ESR signal height.
Figure 4B:
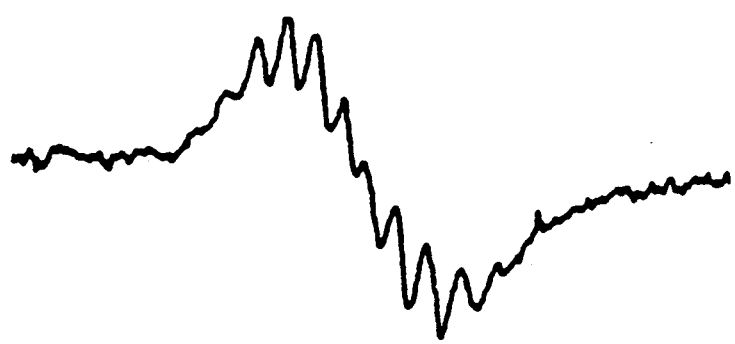
Figure 4C:
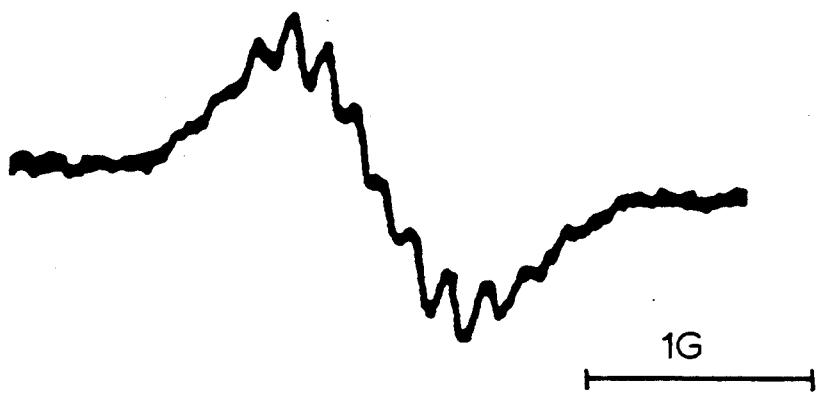

The dramatic change in ESR signal height relative to oxygen tension, as demonstrated in FIG. 3 for the perdeuterated nitroxide spin labels, can be compared to the modest change in signal height relative to oxygen tension for a $1 \times 10^{-4}$ aqueous solution of the fully-hydrogenated CTPO nitroxide spin label, as demonstrated in FIG. 4. The effect of oxygen tension on the signal height of spectra A and B of FIG. 4 is much less dramatic than the signal height effect shown in spectra A and B of FIG. 3, thereby suggesting that a perdeuterated nitroxide spin label would be useful in the detection, measurement and monitoring of a paramagnetic species, like molecular oxygen, in a test sample.

However, the use of the perdeuterated nitroxide spin labels in ESR spectroscopic methods to measure oxygen tension still has disadvantages. Although a strong, sharp, single line spectrum that responds proportionally to the amount of oxygen in the system appears attractive, the perdeuterated spin labels have the disadvantage of contributing to the signal height. Therefore, the signal height is sensitive both to the amount of oxygen in the test sample and to the amount of perdeuterated spin label in the sample. Furthermore, as previously discussed, and as demonstrated in the dashed plot of FIG. 5, although increasing the amount of perdeuterated spin label over low concentrations of spin label increases signal height, an increase in spin label concentration at high concentration levels decreases signal height. Combining this non-linear response of signal height to spin label concentration with a possibility of a non-homogeneous incorporation of the spin label into the test sample, especially in biological test samples, leads to potentially unreliable and inaccurate oxygen tension measurements. A further disadvantage, especially in biological test samples, is the exchange of hydrogen atoms present in the biological sample with any labile deuterium atoms of the perdeuterated spin label. Such hydrogen-deuterium exchange reactions may further complicate the ESR spectrum and make oxygen tension measurements more unreliable.

Therefore, in accordance with an important feature of the present invention, a new class of nitroxide spin labels have been used to enhance the sensitivity of the ESR spectral line width method, or $T_2$ method, of determining the presence and concentration of a paramagnetic species, such as an organic free radical or molecular oxygen, in a test sample, such as a polar or non-polar solution, a living organism, or other biological test sample. The new nitroxide spin labels of the present invention also enhance the ESR spectrometer signal intensity for a given concentration of nitroxide spin label to make concentration measurements of paramagnetic species easier and more reliable than present day ESR spectroscopic methods. In particular, the new class of nitroxide spin labels are used to increase the sensitivity of ESR spectroscopic techniques, utilizing either a standard ESR spectrometer or the low frequency ESR spectrometer disclosed by Halpern in U.S. Pat. No. 4,714,886, herein incorporated by reference, and to provide accurate oxygen tension measurements, from either a polar or non-polar environment, over a broader range of oxygen tensions than is presently possible using the prior art nitroxide spin labels. As will be discussed more fully hereinafter, the new class of nitroxide spin labels of the present invention increases the sensitivity of the ESR spectroscopic technique, and therefore is particularly useful when used in conjunction with the very low frequency ESR spectrometer disclosed by Halpern in U.S. Pat. No. 4,714,886, especially for in vivo applications and for imaging.

The new class of nitroxide spin labels of the present invention are selectively isotopically-labeled nitroxides. Surprisingly and unexpectedly, the selectively isotopically-labeled nitroxides of the present invention not only provide a narrow ESR spectrum that is analogous to the ESR spectrum of perdeuterated spin labels and therefore eliminates much of the signal-to-noise problem, but also demonstrate an appreciably more correctable dependence of ESR spectrum signal intensity from the concentration of the spin label in the test sample, analogous to the ESR spectra of non-deuterated, fully-hydrogenated nitroxide spin labels. Therefore, the selectively isotopically-labeled nitroxides of the present invention provide the benefits afforded by both the fully-hydrogenated nitroxide spin labels and the perdeuterated nitroxide spin labels, and simultaneously eliminates their disadvantages.

The selectively isotopically-labeled nitroxide spin labels of the present invention include stable and inert nitroxide compounds that have more than one non-labile atom of the same identity, wherein at least one, but not all, of the non-labile atoms of the same identity has been replaced by an isotope of that atom. For example, the selectively isotopically-labeled spin labels of the present invention include more than one non-labile hydrogen atom, or more than one non-labile carbon atom, or more than one non-labile oxygen atom, or more than one non-labile nitrogen atom, wherein at least one, but not all, of the non-labile atoms of the same identity has been replaced by an isotope of that atom. For example, if a nitroxide spin label includes three non-labile nitrogen-14 atoms, a selectively isotopically-labeled nitroxide spin label in accordance with the present invention can be achieved by replacing one or two, but not all three, of the non-labile nitrogen-14 atoms with the nitrogen isotope, nitrogen-15, so long as the resulting nitroxide spin label includes at least one nitrogen-14 atom and one nitrogen-15 atom. Similarly, carbon-13 could replace carbon-12 in a nitroxide spin label containing more than one non-labile carbon as long as the resulting selectively, isotopically-labeled spin label includes at least one non-labile carbon-12 atom and at least one non-labile carbon-13 atom. To achieve the full advantage of the present invention, the selectively isotopically-labeled spin label is a partially deuterated nitroxide spin label. Therefore, if a nitroxide spin label includes the number (p) of non-labile hydrogen atoms, a selectively isotopically-labeled spin label of the present invention would include from one to (p-1) number of non-labile deuterium atoms substituted for the non-labile hydrogen atoms.

Furthermore, in accordance with an important feature of the present invention, it is the non-labile atoms of the nitroxide spin labels that are replaced by isotopes of that atom. Labile hydrogen atoms, or labile atoms of any other identity, such as nitrogen or carbon, are not replaced by an isotope of that atom because exchange reactions between a labile moiety on the nitroxide and the test sample would remove the isotopic label from the nitroxide. Therefore, the selective isotopic labeling must be performed on the non-labile moieties of the nitroxide molecule in order to achieve a spin label of the present invention. However, isotopic labeling of a labile moiety usually does not adversely affect the ESR spectroscopic measurements of the method of the present invention, therefore isotopic labeling of a labile moiety can be performed. However, isotopic labeling of only labile moieties will not provide the benefits and advantages of the present invention because the isotopic label will be lost by exchange reactions with the test sample.

When synthesizing the selectively isotopically-labeled nitroxide spin labels of the present invention, it is usually the non-labile hydrogen atoms of the spin label that are replaced by deuterium atoms. However, nitroxide spin label containing all non-labile nitrogen-15 atoms have been synthesized. Therefore, a synthetic route to providing a spin label of the present invention having nitrogen-14 and nitrogen-15 atoms is envisioned. As will be shown more fully hereinafter, the synthetic route used to yield a selectively isotopically-labeled nitroxide spin label of the present invention is novel in that the synthetic route provided a partially-deuterated nitroxide having hydrogen and deuterium atoms situated on the nitroxide spin label molecule at the desired position.

To demonstrate the benefits and advantages of the new class of nitroxide spin labels of the present invention, a member of the class was synthesized according to the novel procedure outlined below. It is apparent that the stable nitroxides of the present invention are secondary amine N-oxides that bear no hydrogen atoms on the carbon atoms attached to the nitroxyl nitrogen, i.e., the alpha and alpha' carbon atoms. The stable nitroxides of the present invention are nitroxides that can be isolated, stored and handled with no more precaution than normally observed when working with most organic substances. If one or more hydrogen or deuterium atoms are present on the alpha or alpha' carbon atoms, the stability of the nitroxide molecule is reduced because such nitroxides can undergo a disproportionation reaction to produce a non-paramagnetic nitrone and a non-paramagnetic N-hydroxyamine that are not observable by ESR spectroscopic techniques. Therefore, it is preferred that both the alpha and alpha' hydrogen atoms are replaced by an inert substituent group, such as an alkyl group containing from one to about ten carbon atoms, and most preferably a methyl group. To achieve the full advantage of the present invention, the four inert substituent groups that replace the hydrogen atoms the alpha and alpha' carbon atoms, such as four methyl substituents, are totally isotopically labeled. Such isotopic labeling provides a nitroxide spin label that gives an ESR spectrum that is more resolved, and therefore easier to interpret. Similarly, in nitroxide spin labels that contain two or more non-labile nitrogen atoms, replacing the naturally-occurring nitrogen-14 isotope by nitrogen-15 may provide a more easily interpreted ESR spectrum because nitrogen-15, having a spin number of ½ gives a simpler two-line spectrum with a large splitting, or line separation, than the three-line spectrum of nitrogen-14 that has a spin number of 1.

Therefore, a preferred selectively isotopically-labeled nitroxide spin label of the present invention has the hydrogen atoms of the alpha and alpha' carbon atoms replaced by perdeuterated methyl groups in order to provide a nitroxide spin label of high stability that generates a relative simple ESR spectrum to interpret. An example of such a nitroxide spin label is the selectively isotopically-labeled spin label, 4-H-perdeuterated CTPO, synthesized according to the following procedure and depicted as structural formula IV:

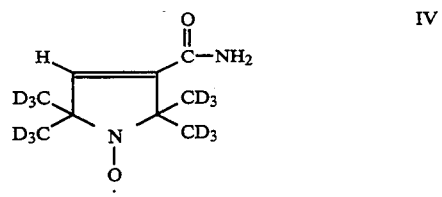

It should be noted that the labile hydrogen atoms on the —CO—NH$_2$ amido group have not been replaced by deuterium atoms, although a deuterium substitution on the amido moiety would not produce any adverse effects. In addition, as preferred, the four methyl substituents on the alpha and alpha' carbon atoms are fully deuterated. The remaining 4-position hydrogen is non-labile and has not been replaced by the deuterium isotope, therefore providing a selectively, isotopically labeled spin label of the present invention.

Synthesis of 3-carbamoyl-2,2,5,5-tetraperdeuteromethylpyrroline-1-yloxyl (4-H-perdeuterated CTPO (IV))

This synthetic procedure is a modification of Rassat's procedure described by R. Chiarelli and A. Rassat in Tetrahedron 29:3639–3647 (1973).

Melting points of solids were determined in Mel-Temp apparatus (Laboratory Devices, Inc., Cambridge, Mass.) with a Pyrex capillary tube and are uncorrected. Infrared (IR) spectra were obtained on a Perkin-Elmer Model 781 double-beam spectrophotometer. Nuclear magnetic resonances (NMR) spectra were determined on a Varian XL-400 instrument using tetramethysilane as the internal reference. Mass spectral (MS) data were obtained on a VG ZAB-SE double-focusing spectrometer, and samples were ionized by fast atom bombardment. Ammonium-d4 chloride is available from Sigma Chemical Co., St. Louis Mo.; acetone-d6 (99.5 atom % D) is available from Aldrich Chemical Co., Milwaukee, Wis.; magnesium oxide (98%, 325 mesh) is available from Alfa Products, Danvers, Mass.; and other chemicals are available from Fisher Scientific Co., Chicago Ill.

A.
2,2,6,6-Tetraperdeuteromethyl-4-oxo-3,5tetradeuteropiperidine (Triacetoneamine-d$_{16}$) (V)

A mixture of ammonium-d$_4$ chloride (3.45 g, 0.06 mole), acetone-d$_6$ (99.5 atom %D, 12.5 ml, 0.15 mole), anhydrous sodium carbonate ( 3.18 g, 0.03 mole) and magnesium oxide (3.0 g) was added to a 250 ml round-bottomed flask. The flask was capped with a rubber septum and wired, then the reaction mixture heated in an oil-bath at 50° C. for 3 days. After cooling, 20 ml of acetone was added to the reaction mixture and the resulting mixture was filtered. The recovered solid was crushed into powder, washed with 15 ml of acetone and then filtered with suction filtration. The combined filtrates were concentrated to dryness. The resulting red liquid (7.2516 g) was distilled under reduced pressure to obtain 4.7480 g (56.7%) of a bright yellow liquid (b.p. (boiling point) 54°–55° C./1.9 mm Hg) that solidified when chilled in a dry ice/acetone bath. The solid product subsequently was used without further purification. Recrystallization of an analytical sample from anhydrous diethyl ether yielded white crystals, mp. 57°–58° C. [lit. 58° C.]; IR(KBr, cm$^{-1}$):3580(m), 3260(m), 2220(m), 1700(s), 1530(w), 1265(s), 1140(m), 1050(m), 930(w); $^{13}$C-NMR (CDCl$_3$): 31.03(m), 53.50(m), 54.88(s), 211.19 (s).

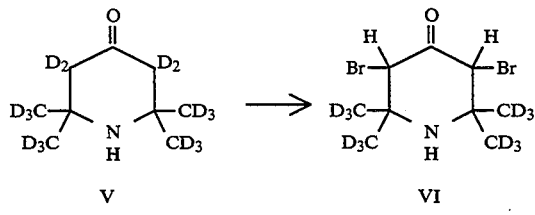

B.
3,5-Dibromo-2,2,6,6-tetraperdeuteromethyl-4-oxopiperidine hydrobromide (VI)

Triacetoneamine-d$_{16}$ (V) (4.0519 g, 23.7 mmol) was dissolved in glacial acetic acid (16 ml), and the mixture was cooled in an ice bath. A solution of bromine (8.1348 g, 2.62 ml) in 10 ml of acetic acid was slowly added to the stirred solution of triacetoneamine-d$_{16}$ (V). After the addition of the bromine solution was completed, the resulting reaction mixture was stirred at room temperature for 22 hours. A precipitate that formed was collected by suction filtration, then washed successively with acetic acid, water and diethyl ether. The precipitate then was air dried to yield 7.1199 g (74%) of a white powder having an mp of 180°–191° C. The white powder, when treated with aqueous ammonia and potassium hydroxide, was found to be a mixture of 3,5-dibromo-3,5-dideutero-2,2,6,6-tetraperdeuteromethyl-4-oxopiperidine hydrobromide, 3,5-dibromo-3-deutero-2,2,6,6-tetraperdeuteromethyl-4-oxopiperidine hydrobromide and 3,5-dibromo-2,2,6,6-tetraperdeuteromethyl-4-oxopiperidine hydrobromide as shown by a $^{13}$C-NMR of 2,2,5,5-tetraperdeuteromethylpyrroline-3-carboxyamide.

The white powder (0.3240 g, 0.79 mmol) was stirred in a mixture of 5 ml of 1N hydrogen bromide and 5 ml of acetic acid at room temperature for 11 days. The resulting precipitate was filtered to yield 0.1457 g of the solid compound VI. The filtrate was concentrated, filtered, then washed with 1 ml water and then with anhydrous diethyl ether to give an additional 0.0544 g of the solid compound VI. The total yield of compound VI was 0.2001 g (62.1%).

C.
2,2,5,5-Tetraperdeuteromethylpyrroline-3-carboxyamide (VII)

To a stirred suspension of 3,5-dibromo-2,2,6,6-tetraperdeuteromethyl-4-oxopiperidine hydrobromide (VI) (0.1457 g, 0.36 retool) in 1.5 ml 28% aqueous ammonia was added a sufficient amount of solid potassium hydroxide to saturate the suspension. The resulting reaction mixture was stirred overnight at ambient temperature, then carefully neutralized with 1N hydrochloric acid. The resulting solution was extracted 3 times with 10 ml fractions of chloroform, dried over anhydrous sodium sulfate, and then evaporated to yield 0.0506 g (78.3%) of a white solid, mp 183°–185° C.; IR(KBr, cm$^{-1}$):3360(m), 3200(m), 2220(w), 1665(s), 1645 (s), 1605 (s), 1415 (m), 1170 (w), 1060 (w); 13C-NMR (CDCl$_3$): 29.20(m), 63.02(s), 66.33(s), 142.06(s, 2C), 167.22(s); mass spectrum (MS):181(M+1), 180(M), 162(M-CD$_3$).

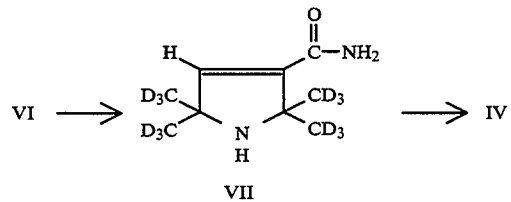

D.
3-Carbamoyl-2,2,5,5-tetraperdeuteromethylpyrroline-1-yloxyl (IV)

To a solution of 0.0310 g (0.17 mmol) 2,2,5,5-tetraperdeuteromethylpyrroline-3-carboxyamide (VII) in 1 ml of water was added ethylenediaminetetraacetic acid tetrasodium salt (0.0050 g, 0.013 mmol), sodium tungstate dihydrate (0.0050 g, 0.015 mmol) and 30% hydrogen peroxide (0.08 ml). The resulting reaction mixture was left in the dark for 4 days. The yellow crystals that formed were filtered. The filtrate then was acidified with 1N hydrochloric acid and extracted with chloroform. The chloroform extract was dried over anhydrous sodium sulfate, filtered, and then evaporated to dryness. The total yield of the nitroxyl compound (IV) was 0.0255 g (76%):mp 203°–204° C. (dec.); IR(KBr, cm$^{-1}$):3400(m), 3180(m), 2230 (w), 1670 (s), 1630 (m), 1420 (m), 1320 (w), −1150 (w), 1100 (w), 1040 (w); mass spectrum (MS): 197 (M+2), 196 (M+1), 195 (M), 181 (M+2-NH$_2$) .

It has been found that the partially-deuterated nitroxide spin label (IV), selectively hydrogenated at the 4-position of the nitrogen heterocyclic ring, surprisingly and unexpectedly enhances the sensitivity of an ESR spectroscopic method to detect, measure and monitor the oxygen tension of a test sample. The nitroxide spin label of structural formula IV provides a narrow ESR spectrum, therefore eliminating most of the usual signal-to-noise problems, and provides an ESR spectrum that is substantially less sensitive to the concentration of selectively, isotopically-labeled spin label added to the test sample. In addition, the partially-deuterated CTPO spin label of structural formula IV has not only provided an ESR spectrum that is relatively narrow and that is measurably and correctably dependent on the amount of spin label in the test sample and is independent of the height of the spectrum, but also reflects the oxygen concentration of the test sample.

For oxygen-free test samples, the 4-H-perdeuterated CTPO of structural formula IV gives a well-resolved, two-line ESR spectrum rather than the thirteen-line ESR spectrum observed for the fully-hydrogenated CTPO spin label of structural formula II. It has been theorized that the well-resolved ESR spectrum of the partially-deuterated CTPO of structural formula IV, and the subsequent broadening of the two lines of ESR spectrum in the presence of oxygen, is caused by two independent sources. First, the width of the perdeuterated TEMPONE (structural formula III) spectrum, at a concentration of $2 \times 10^{-4}$ TEMPONE, under anoxic conditions (i.e., no oxygen present in the test sample) is approximately 13 microtesla. However, in the ESR spectrum of the 4-H-perdeuterated CTPO of structural formula IV, the splitting of the ESR spectral line, induced by the hydrogen at the 4-position, has been measured by electron nuclear double resonance and found to be 40 microtesla. Therefore, the broadening of the perdeuterated line by the 4-position hydrogen by a factor of from about 2 to about 3 makes the splitting induced by the 4-position hydrogen an ideal oxygen measure. As a result, and as will be discussed more fully hereinafter, for a pure absorption ESR spectrum of a solution of 4-H-perdeuterated CTPO (IV) under oxygen-free conditions consisting of two well-resolved spectral lines, the introduction of oxygen into the solution provides an ESR spectra that fills the dip, or valley, between the two spectral lines, as demonstrated in FIG. 6. The corresponding, and more useful, derivative ESR spectra are shown in FIG. 7.

Therefore, because the 4-H-perdeuterated CTPO nitroxide of structural formula IV has a two line hyperfine ESR spectral signal, using the compound of structural formula IV in an ESR spectroscopic technique to assay a test sample for a paramagnetic species provides the advantage of allowing the spectrometer field, or the frequency, modulation to be reduced only by a factor of 2 in relative to the modulation needed to detect the unresolved hyperfine spectrum with low distortion in order to resolve the hyperfine lines. Reducing the modulation by a factor of 2 can be compared to the necessity of reducing the modulation of the spectrometer by a factor of 13 in order to resolve the proton hyperfine lines of fully-hydrogenated CTPO. Stated in alternative terms, by having to reduce the field modulation only by a factor of 2 rather than by a factor df 13, six and one-half times more of the spin label added to the test sample is contributing to the intensity of the spectrum signal. Therefore, the selectively isotopically-labeled nitroxide of the present invention can provide a stronger, well-resolved hyperfine ESR spectra, that is more easily measured, and therefore provides more accurate and reliable data.

When using the selectively isotopically-labeled compounds of the present invention, especially the monohydrogenated perdeuterated nitroxide spin labels, in an ESR spectroscopic technique to detect and measure the presence of a paramagnetic species, like molecular oxygen, in a test sample, the absorption ESR spectrum shows an increase in the region of overlap of the two spectral lines as oxygen tension increases. As demonstrated in FIG. 6, when the spectral lines broaden in response to the increase in oxygen tension, the valley in the two-line hyperfine absorption ESR spectrum rises dramatically because the subtle line-broadening effects produced by an increase in oxygen tension are magnified by the steep slope of the two overlapping hyperfine lines. This effect is demonstrated in FIG. 6 wherein it is shown that an increase in oxygen tension produces a spectral line broadening that quickly fills the valley between the two absorption peaks of the ESR spectrum.

The line-broadening effect of increased oxygen tension on an absorption ESR spectrum is seen as a dramatic reduction in the amplitude of the middle trough/peak complex in a corresponding derivative ESR spectrum, as shown in the two spectra of FIG. 7. The line-broadening, trough-filling and amplitude effects observed in a derivative ESR spectrum may be attributed to machine operating conditions, but such operating conditions are readily controlled and monitored should corrections be necessary. However, overall, it has been demonstrated that the ESR spectra of the selectively isotopically-labeled spin labels of the present invention are sensitive to a variation of the oxygen tension of the test sample, and that this sensitivity to oxygen tension can be observed, and quantified, to provide useful information concerning the amount, identity and/or surrounding environment of a paramagnetic species in a test sample. In general, evidence of hypoxia, or lack of oxygen, therefore is simplified by using a selectively isotopically-labeled spin label rather than a fully-hydrogenated spin label. As will be discussed more fully hereinafter, this simple line-broadening or signal amplitude effect on the two-line hyperfine ESR spectrum of the selectively-isotopically labeled compound of structural formula IV therefore simplifies the interpretation of data gathered from the multiple gradient scans that are used in image reconstruction.

Figures 8A, 8B, 8C:
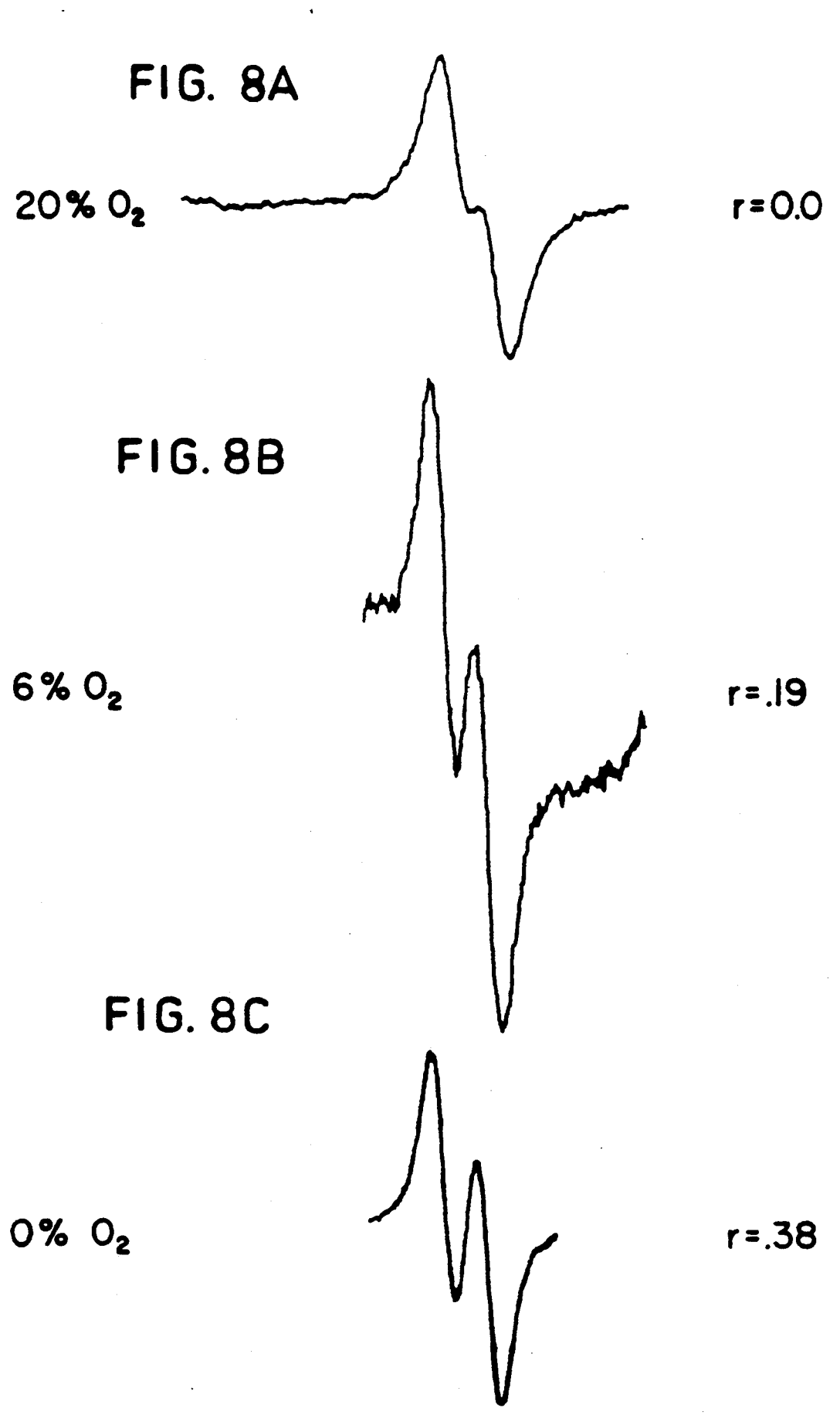

To show the line width-broadening and amplitude-altering effect of increased oxygen tension on the ESR spectrum-of 4-H-perdeuterated CTPO (IV), ESR derivative spectra of aqueous solutions of 4-H-perdeuterated CTPO having increasing concentrations of molecular oxygen were obtained. The ESR spectra are shown in FIG. 8, wherein it is demonstrated that the spectral lines broaden with increasing oxygen concentration, and that the value of the parameter r, similar to the previously defined parameter K, decreases with increasing oxygen concentration. The parameter r, depicted visually on the derivative ESR spectra of FIG. 7, is defined as the ratio of the amplitude of the central trough/peak complex of the derivative ESR spectra, designated as (b), of FIG. 7 to the amplitude of the outer, flanking major trough/peak complex, designated as (a), of the derivative ESR spectra.

The spectra illustrated-in FIG. 8 show only the central nitrogen line from the same aqueous sample, containing $2 \times 10^{-4}$M of 4-H-perdeuterated CTPO, and equilibrated with a gas containing various proportions of oxygen and 99.4% pure nitrogen. The proportions of oxygen and nitrogen were determined using rotometer flowmeters to adjust and measure the component gas flow rates before the gases were combined. The combined gases were bubbled through stopper sealed samples of the aqueous 4-H-perdeuterated CTPO solution for two hours, with frequent shaking. The ESR spectra then were measured at 31° C. Qualitatively, the ESR spectra in FIG. 8 and the calculated r values show that the parameter r decreases as oxygen tension increases. However, surprisingly and unexpectedly, it has been found that the parameter r also decreases quantitatively with increased oxygen tension when a selectively isotopically-deuterated spin label of the present invention, such as 4-H-perdeuterated CTPO, is used in an ESR spectroscopic technique to measure oxygen tension. In analyzing the ESR spectrum presented in FIG. 8, it also should be noted that oxygen tension can be measured independently of the overall amplitude of the ESR spectrum, but is proportional to the parameter r. The solution containing 6% oxygen gave an ESR spectrum of greater amplitude than the solutions containing 0% and 20% oxygen, however, the parameter r is reduced as oxygen concentration increases.

To show the sensitivity of an ESR spectrum of a test sample containing a selectively isotopically-labeled spin label of the present invention to oxygen tension, and to show the measurable and correctable dependence of the ESR spectra and oxygen tension measurements on the amount of isotopically-labeled spin label in the test sample, the ESR spectra of a series of aqueous solutions containing amounts of 4-H-perdeuterated CTPO (IV) ranging from about $0.5 \times 10^{-4}$M to about $10 \times 10^{-4}$M, and having an oxygen tension ranging from 0 to about $20 \times 10^{-4}$ molar was taken. The ESR spectra were taken on a low frequency ESR spectrometer, disclosed by Halpern in U.S. Pat. No. 4,714,886, that operates below 1 GHz and is designed for in vivo ESR measurements. This low frequency spectrometer can measure large samples, such as about 10 ml, making the low frequency spectrometer ideal for this particular experiment, and for in vivo applications in general. Ten scans of the test sample was sufficient to provide an ESR spectrum. The data from the ESR spectra obtained by this method is plotted in FIG. 9.

Figure 9:
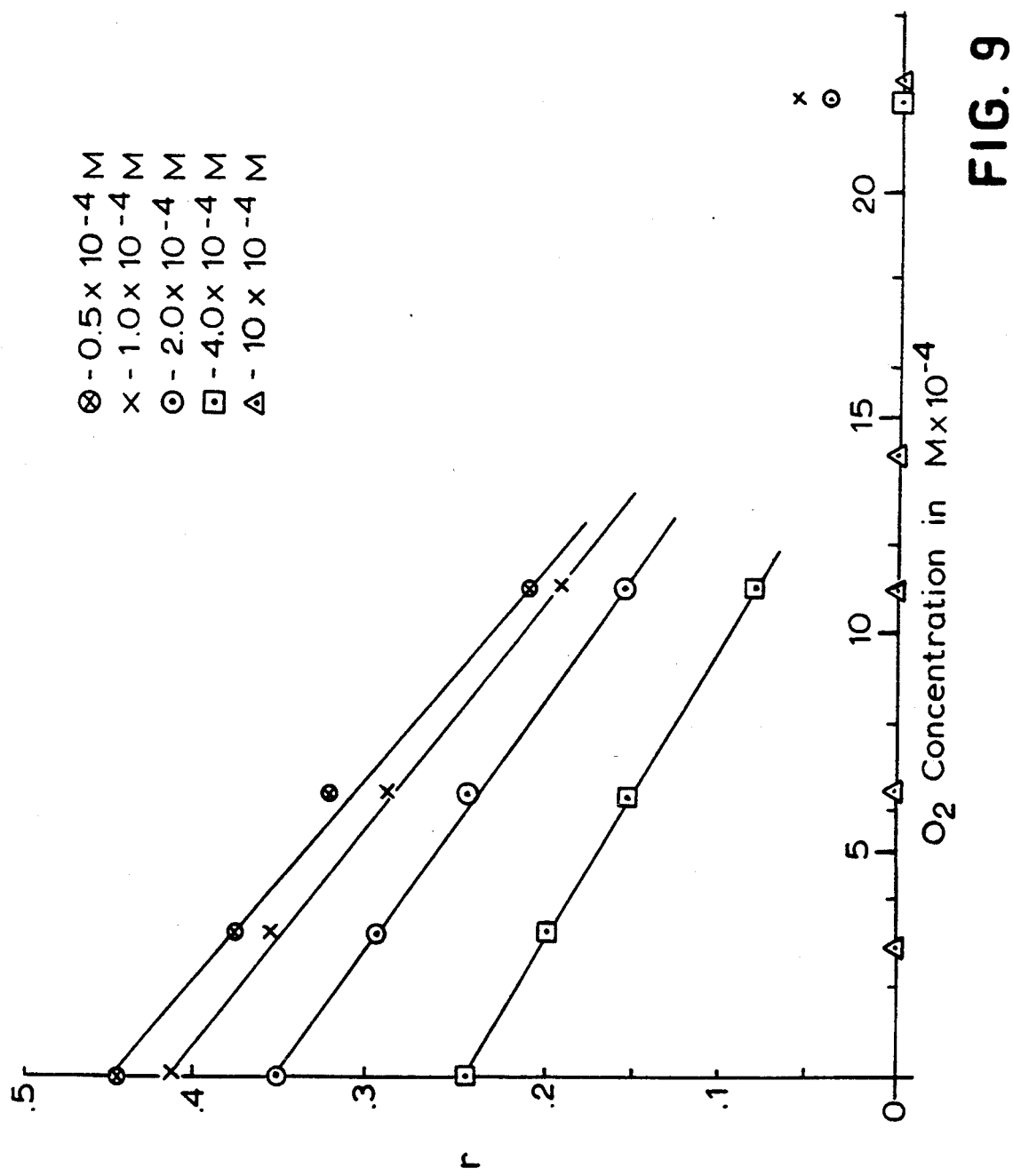
FIG. 9 is a series of graphs showing the essentially linear relationship between oxygen tension and the parameter r, and determined over a concentration of from about $0.5 \times 10^{-4}$ to about $10 \times 10^{-4}$M of the selectively isotopically-labeled nitroxide spin label.

FIG. 9 therefore is a series of graphs showing the essentially linear relationship between the parameter r, calculated from the derivative ESR spectrum of a test sample, and the oxygen tension of a test sample. The series of graphs of FIG. 9 further shows a linear relationship between the parameter r and oxygen tension over a range of spin label concentrations in the test sample ranging from $0.5 \times 10^{-4}$ to $10 \times 10^{-4}$M perdeuterated CTPO (IV). It should be noted that the spin label concentration can vary by a factor of at least 8 and the r parameter will vary by a correctable factor of 25%. It also should be noted that at spin label concentrations substantially above $4 \times 10^{-4}$M, like $10 \times 10^{-4}$M, that a loss in r parameter sensitivity to oxygen tension occurs.

For example, from FIG. 9, if a test sample includes $1.0 \times 10^{-4}$M of the selectively isotopically-labeled compound IV, a linear relationship between the parameter r and oxygen tension is found over parameter r values ranging from over 0.4 to about 0.1 and over oxygen tensions ranging from 0 to about $14 \times 10^{-4}$M. Some non-linearity is found at oxygen tensions above about $20 \times 10^{-4}$M due to the approach of the parameter to its lower limit, the value of zero. A similar linear relationship between oxygen tension and the parameter r is found for test samples that include $0.5 \times 10^{-4}$M, $2.0 \times 10^{-4}$M, $4.0 \times 10^{-4}$M and $10 \times 10^{-4}$M 4-H-perdeuterated CTPO (IV), although r parameter sensitivity is reduced and eventually lost when high concentrations of selectively isotopically-labeled spin label are added to the test sample.

Figure 5:
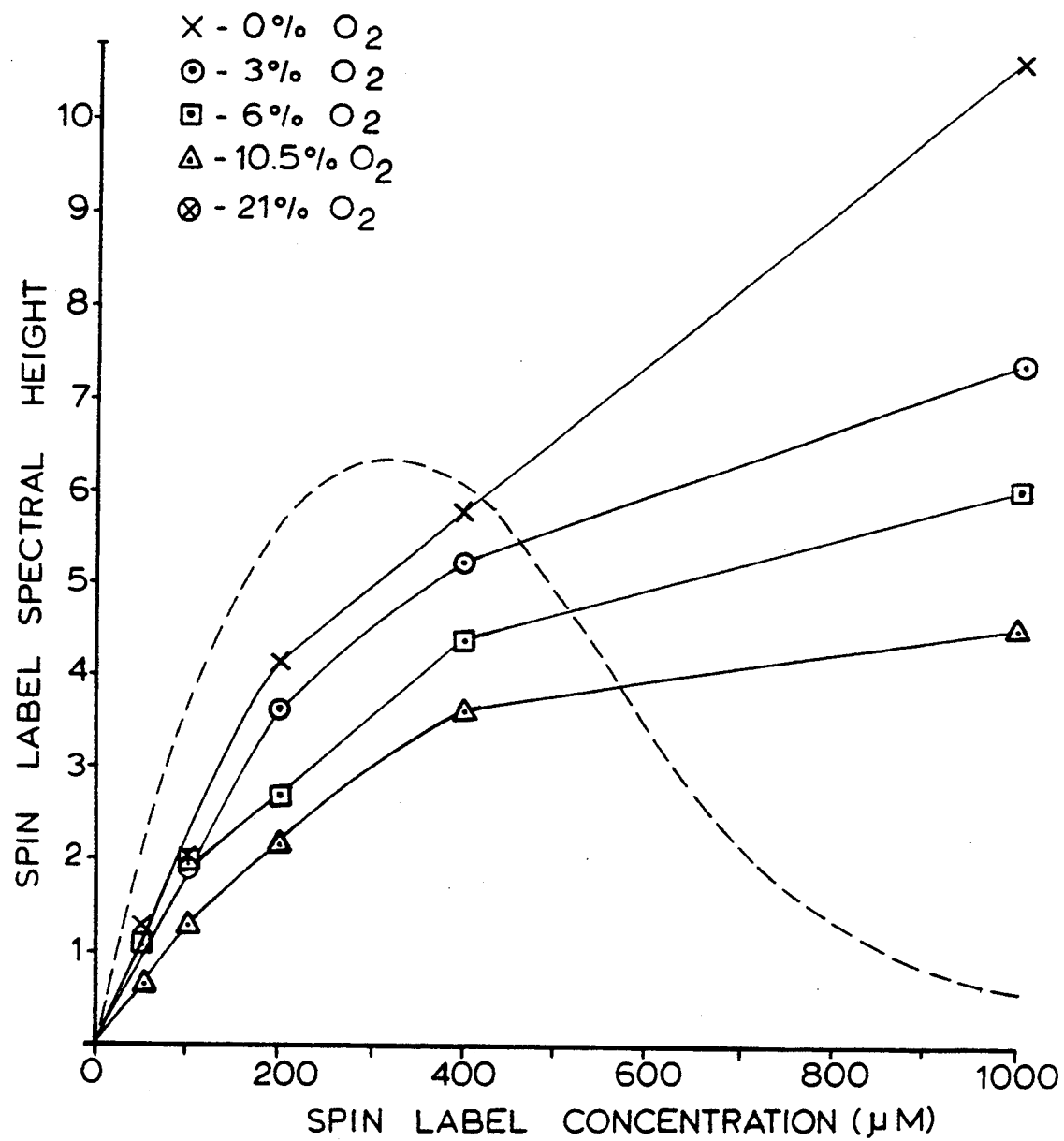
FIG. 5 is a series of graphs showing the variation of ESR spin label spectral height vs. spin label concentration at varying oxygen tensions.

From FIG. 5, it is seen that the concentration of the nitroxide spin label of the present invention present in the test sample affects ESR spectral height in an essentially linear fashion as spin label concentration increases over a broad range. Therefore, unlike the perdeuterated TEMPONE spin label (III), that acts to increase spectral height at low spin label concentrations and decrease spectral height at high spin label concentrations (i.e., the dashed line plot of FIG. 5), the selectively isotopically-labeled spin labels of the present invention allow correlation of spectral height to spin label concentration, that in turn can be used as a correction factor when determining the oxygen tension of test samples that may contain different concentrations of spin label compound. Such corrections cannot be made reliably with the perdeuterated spin label compounds of the prior art.

Therefore, because the selectively isotopically-labeled spin labels of the present invention provide ESR spectra that are measurably and correctably dependent on spin label concentration in the test sample and that are essentially independent of the operating conditions of the ESR spectrometer, an easy and reliable method to determine oxygen tension in a non-oxygen consuming test sample by ESR spectroscopic techniques is available by first preparing a calibration curve. The calibration curve is prepared by first adding a known amount of a spin label of the present invention to a standard sample, followed by oxygenating the standard sample containing a known amount of a spin label of the present invention to a known oxygen tension, then obtaining an ESR spectrum of the oxygenated standard test sample, and finally determining the r parameter from the ESR spectrum. Repeating the above procedure on a series of standard test samples, each including the identical amount of a spin label of the present invention and each oxygenated to a different oxygen tension would provide an essentially linear graph of r parameters vs. oxygen tension. Then, by determining the r parameter of an ESR spectrum of a test sample of unknown oxygen tension by the identical procedure, the unknown oxygen tension of the test sample can be accurately and reliably determined from the essentially linear graph.

Similarly, the oxygen tension of an oxygen consuming test sample, like a living organism, can be determined. Living organisms can metabolize or excrete a spin label compound, therefore spin label concentration may not remain constant over a time span of several hours after addition of the spin label. Therefore, like the procedure described above, the oxygen tension of a living biological sample can be determined from a linear standard, calibrated graph after the spin label concentration first is determined from the height of the ESR spectrum. Then, a correction could be made by using plots, such as in FIG. 5, to adjust oxygen tension measurements from the apparent oxygen tension measurement made at the spin label concentration at that particular time to the actual oxygen tension at a standard, constant spin label concentration.

Overall, the selectively isotopically-labeled nitroxide spin labels of the present invention increase the sensitivity of the ESR spectrum of a particular environment by maximizing the sensitivity of the $T_2$ spectrum line-broadening method to oxygen tension and by optimizing the sensitivity of the spectrometer signal for a given concentration of spin label. It should be noted, however, that although the particular advantages presented by the compound of the present invention, 4-H-perdeuterated CTPO, in regard to ESR oxymetric measurements, namely that the compound of structural formula IV contains one non-labile hydrogen atom and twelve non-labile deuterium atoms and that the compound has high water solubility, is not meant to limit the scope of the present invention to the particular selectively isotopically-labeled spin label of structural formula IV, or to limit the use of the spin label compounds of the present invention to ESR oxymetric measurements.

The selectively isotopically-labeled compounds of the present invention can be designed and synthesized to provide the desired ESR spectrum, such as peak height or coupling constant, for the particular paramagnetic species or the particular environment, i.e., aqueous solution or biological sample, of interest. The 4-H-perdeuterated CTPO (IV) described above was synthesized because it was determined that an ideal spin label for an ESR oxymetric method would provide an ESR spectrum that is a doublet, with peaks properly spaced apart in the absence of oxygen to give a deep valley. Therefore, the spin label of interest would need a coupling constant of approximately 450 milligauss. As a result, in the design of a suitable spin label for an oxymetric ESR method, the placement of a hydrogen atom at the 4-position of perdeuterated CTPO was important because the 4-position hydrogen set the spectral lines the correct distance apart to obtain a good ESR measurement of line broadening caused by increased oxygen concentration. Therefore, having designed a compound that would give a two-line ESR spectrum, with a sufficient amount of splitting to separate the lines, the compound, 4-H-perdeuterated CTPO was synthesized. Other selectively isotopically-labeled nitroxide spin labels can be designed and synthesized according to desired spectral properties and the test sample environment to be assayed.

For example, the 4-H-perdeuterated CTPO (IV) is relatively highly water soluble. Therefore, the compound of structural formula IV has found use in ESR oxymetric measurements of aqueous solutions. However, it is envisioned that the hydrophilic carbamoyl moiety of 4-H-perdeuterated CTPO can be substituted with, or replaced by, a more lipophilic moiety such that ESR measurements for oxygen tension, or for other free radical species, can be made in non-aqueous solutions or within living cells. A compound of structural formula (IV) can be made more lipophilic, such that the compound can more easily enter a living cell, by including a lipophilic moiety on the compound during the synthesis of the selectively isotopically-labeled spin label, or by performing reactions on a reactive functional group present on the selectively isotopically-labeled spin label, such as the carbamoyl group, in order to introduce lipophilic substituents onto the selectively isotopically-labeled spin label.

As a result, it is envisioned that an investigator can design a nitroxide that incorporates a suitable hydrophilic or lipophilic moiety in order to effectively study the particular environment of interest, such as an aqueous solution or a biological sample. After determining the desired hydrophilicity or lipophilicity of the nitroxide spin label, the investigator then must determine the number and positions of non-labile atoms of a particular identity to selectively isotopically label, i.e., how many non-labile hydrogen atoms should be replaced by deuterium atoms and at what position in the nitroxide molecule should selective isotopic labeling be made in order to properly position the hyperfine spectral lines of the ESR spectrum, i.e., a suitable coupling constant, such that meaningful and accurate data from the ESR spectrum can be derived.

Therefore, in accordance with an important feature of the present invention, modifying the novel synthetic route for the 4-H-perdeuterated CTPO (IV) can yield a compound of general structural formula VII:

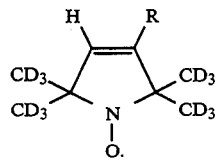

VII wherein the moiety R can be any of a variety of lipophilic or hydrophilic moieties that alter the physical and/or chemical characteristics of the selectively isotopically-deuterated spin label to allow investigation of paramagnetic species in different environments, such as an aqueous environment, non-aqueous environment, or within a living cell. The moiety R can be any organic moiety that is stable when bound to a vinyl carbon atom. For example, the moiety R can be, but is not limited to: amido (—CO—NH$_2$); cyano (—CN); hydroxymethyl (—CH$_2$OH); bromomethyl (—CH$_2$Br); alkylcarbonyl or arylcarbonyl (—CO—R'), wherein R' is an alkyl, substituted alkyl, aryl or substituted aryl group; alkoxycarbonyl or arylcarbonyl (—CO—OR'); substituted amido carbonyl (—CO—NHR'); alkyl, substituted alkyl, aryl or substituted aryl (—R'); alkoxy or aryloxy (—OR'); isothiocyanato (—NCS); or thiocyanato (—SCN).

In addition, ESR spectroscopic inventions have shown that free radicals are generated, then decay, in oxidations initiated by enzymes. Therefore, it is envisioned that the R moiety of the compound of structural formula VII can be designed such that the nitroxide spin labels of the present invention can bond to an enzyme, or to DNA, in order to investigate different environments for the presence and concentration of free radical species. For example, the amido group of the compound of structural formula IV can be bound to, or can be modified such that it can bond to, an active site of an enzyme or DNA. Likewise, a nitroxide spin label of the present invention can be designed with a suitable R moiety such that the spin label can bond to a nucleotide, cofactor, prothetic group or sugar in order to investigate different environments of a biological sample. In addition, compounds such as adenosine triphosphate and choline chloride can be bound to nitroxide spin labels of the present invention in order to investigate the biological environment where such compounds operate.

The selectively isotopically-labeled spin labels of the present invention can be designed to react and bond to enzymes and the like by activating the spin label by placing a suitable reactive functionality on the R moiety of the compound of structural formula VII through chemical techniques such as acylation, sulfonylation or phosphorylation. The particular reactive functionality placed on the R moiety will depend upon the particular binding site that is available in the environment of interest. The reactive functionality R will be one that can bind to the binding site available in the environment of interest. One example is the flourophosphonation of a nitroxide spin label such that the resulting spin label will selectively bond to the active sites of serine enzymes, such as acetylcholinesterase.

Similarly, the selectively, isotopically-labeled spin labels of the present invention are not limited to a particular spin label, like 4-H-perdeuterated CTPO (IV). The spin label compound of the present invention can be any organic spin label compound that possess a stable paramagnetic moiety like the nitroxyl moiety, and that is selectively and partially isotopically-labeled to provide a spin label compound demonstrating the particular physical and chemical properties required to investigate the particular paramagnetic species and/or the particular environment of interest. For example, other suitable spin label compounds that can be selectively isotopically-labeled to provide a spin label of the present invention include, but are not limited to:

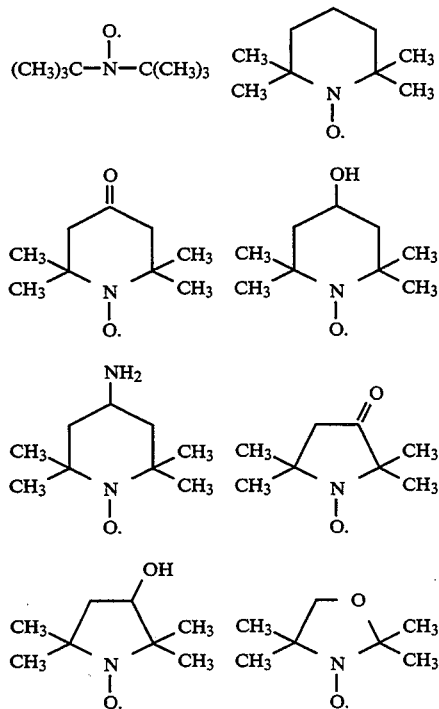

It should be realized that this illustrative list of nitroxides can be further substituted, either directly on the nitrogen heterocyclic ring or on a heterocyclic ring substituent to alter the physical and chemical properties of the spin label such that the spin label possesses the physical and chemical properties needed for the particular assay of interest.

The increase in sensitivity of an ESR spectroscopic method to accurately determine the oxygen tension of a test sample provided by the selectively isotopically-labeled spin labels of the present invention has important medical applications. For example, such a reliable and accurate oxymetric technique has applications in the study and diagnosis of ischemic, i.e., blood deficiency, diseases, such heart attacks and strokes. However, it also should be noted that the selectively isotopically-labeled spin labels of the present invention can be used in ESR spectroscopic techniques to detect, measure and monitor other paramagnetic species in addition to molecular oxygen. For example, the spin labels of the present invention can be used in an ESR technique to detect, measure and monitor organic free radicals, and therefore can trace the free radical metabolites of drugs administered to living organisms. In addition, the ESR spectra of nitroxides are sensitive not only to molecular motions, but also to the nature of the environment that the nitroxide is dissolved. As a result, the spin label compounds of the present invention also can be used to measure the viscosity of various locales within a living organism because variations in viscosity effect spin states, and that in turn effects ESR spectrum line widths. Furthermore, density and other physical and chemical characteristics, in addition to oxygen tension and viscosity, of the spin label environment can be made because of the enhanced sensitivity of ESR spectroscopic method provided by the class of compounds of the present invention.

In accordance with another important feature of the present invention, the selectively isotopically-labeled spin labels of the present invention increase the sensitivity of ESR spectroscopic techniques. Such increases in sensitivity are particularly advantageous when using low frequency ESR spectrometers, such as ESR spectrometers that operate at below 1 GHz, that generate a less intense signal than ESR spectrometers that operate at frequencies greater than 1 GHz. Usually, ESR spectrometers operate at from about 1 GHz to about 10 GHz, the X-band. However, at these high frequencies, the radio frequency does not penetrate the aqueous sample to any appreciable extent, thereby making measurements of the deep portions of the sample difficult. However, at low frequencies, such as below about 1 GHz, the radio frequency can penetrate the deep portions of the sample to provide an accurate measurement within these deep portions and to reduce the distortions of the image of the deep portions of the sample observed at high operating frequencies. Therefore, the selectively-isotopically labeled spin labels of the present invention will enhance the sensitivity of ESR assays for a paramagnetic species in a test sample, including living organisms, especially when using a low frequency ESR spectrometer, such as that disclosed by Halpern in U.S. Pat. No. 4,714,886.

The increased sensitivity provided by the selectively isotopically-labeled spin labels of the present invention, that in turn enhances the use of a low frequency ESR spectrometer to assay a test sample for a paramagnetic species, is important in several respects. For example, the standard ESR spectrometer is unsuited for making whole or partial body measurements of live, small mammals at the operating frequencies of the standard ESR spectrometer (10 GHz) because the measurements are sensitive to the competing absorption of energy by water. Therefore, either the test sample volume must be small, typically about 50 ul (microliters), or the frequency of the ESR spectrometer must be reduced such that the absorption of electromagnetic energy by water also is reduced. However, using a lower frequency also reduces the strength of the ESR signal. Accordingly, due to the increased sensitivity provided by the selectively isotopically-labeled spin labels of the present invention, a low frequency ESR spectrometer can be used more efficiently because a sufficiently stronger ESR signal results such that measurements as to the presence and concentration of a paramagnetic species in the test sample can be made more accurately. In addition, by increasing the sensitivity of ESR techniques, the spin label compounds of the present invention make it possible to test relatively large test sample volumes, such as 10 ml, therefore allowing the selectively isotopically-labeled spin labels of the present invention to be used for in vivo measurements, especially in conjunction with a low frequency ESR spectrometer, to improve assay reliability.

The low frequency ESR spectrometer can measure ESR signals of a spin label from large quantities of cells (in vitro) and from live animals (in vivo). In an in vitro experiment, a spin probe is mixed into a cell suspension and the ESR spectrum of the resulting suspension is taken. In an in vivo experiment, the live animal is injected with a physiologically-acceptable solution of the spin label, and an ESR spectrum is taken of the particular portion of the animal that is of interest. In addition, the selectively isotopically-labeled spin labels of the present invention enhance the sensitivity of ESR measurements. Consequently, it is possible to answer the question frequently raised in assessing the utility of ESR measurements of biological systems of whether an in vitro measurement reflects the actual situation in vivo. To date, a large number of ESR measurements have been made on excised tissue or cell suspensions (in vitro) trying to correlate the presence of absence of a paramagnetic species with a metabolic condition or disease state, e.g., cancer. In accordance with an important feature of the present invention, conducting such ESR measurements in vivo, and using the selectively isotopically-labeled compounds of the present invention, provides more reliable and realistic data.

To date, the practical application of in vivo ESR measurements have been limited. The low frequency ESR spectrometer disclosed by Halpern in U.S. Pat. No. 4,714,886 provided a spectrometer capable of effectively penetrating and making accurate measurements within a deep portion of the test sample. However, low frequency spectrometers inherently lead to some sacrifice in sensitivity. Therefore, the sensitivity enhancement provided by the selectively isotopically-labeled compounds of the present invention provides an ESR spectroscopic technique to detect, measure and monitor the presence of a paramagnetic species in vivo. Surprisingly and unexpectedly, the selectively isotopically-labeled nitroxide spin labels of the present invention provided the increased sensitivity needed to perform non-invasive, in vivo ESR measurements, especially when used in conjunction with a low frequency ESR spectrometer. By using the class of compounds of the present invention as the spin label, such ESR measurements are easily repeatable and provide more accurate and reliable data than prior art in vivo ESR measurements.

Therefore, the spin label compounds of the present invention can be used With a low frequency ESR spectrometer to produce, noninvasively, a highly resolved ESR spectrum that can detect, measure and monitor a paramagnetic species in a living organism. For example, the enhanced sensitivity to ESR spectroscopic procedures provided by the spin labels of the present invention permit the differentiation between normal tissue and a tumor by imaging techniques. The imaging techniques using the low frequency ESR spectrometer are described in Halpern U.S. Pat. No. 4,714,886 and hereby incorporated by reference. The ESR imaging technique is improved by the enhanced sensitivity to paramagnetic species provided by the selectively isotopically-labeled spin labels of the present invention. For example, using a selectively isotopically-labeled spin label provides accurate and reliable quantitative data on the oxygen tension in living tissue by ESR spectrum line broadening.

Therefore, the novel class of nitroxide spin label compounds of the present invention are selectively isotopically-labeled and are used to increase the sensitivity of ESR measurements for paramagnetic species in a test sample. The class of compounds of the present invention have been found particularly useful in ESR spectroscopic methods to determine oxygen tension. The increase in sensitivity of the ESR measurement provided by the selectively isotopically-labeled spin labels of the present invention allows increased use of ESR spectroscopic techniques in the chemical and medical fields by allowing a more accurate and reliable detection, measurement and monitoring of a paramagnetic species, either in solution or in a biological sample, like a living organism, by nondestructive and noninvasive techniques, using either a standard or a low frequency ESR spectrometer.

Obviously, many modifications and variations of the invention as hereinbefore set forth can be made without departing from the spirit and scope thereof and therefore only such limitations should be imposed as are indicated by the appended claims.

We claim:

1. A spin label compound having an electron spin resonance spectrum that is detectably and measurably broadened by the presence of a paramagnetic species and having the structural formula:

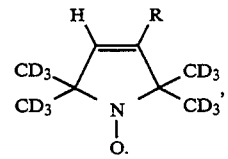

wherein R is selected from the group consisting of amido (—CO—NH$_2$); alkylcarbonyl, carbocyclic arylcarbonyl (—CO—R′); alkoxycarbonyl, aryloxycarbonyl (—CO—OR′); and substituted amido carbonyl (—CO—NHR′), wherein R′ is an alkyl, substituted alkyl, carbocyclic aryl or substituted carbocyclic aryl group.

2. The spin label compound of claim 1 having the structural formula:

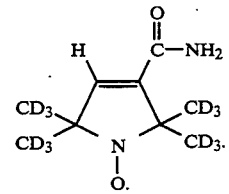

3. A composition capable of exhibiting a broadened electron spin resonance spectrum upon interaction with a paramagnetic species to show the presence or concentration of the paramagnetic species in a test sample, said composition comprising a sufficient amount of a spin label compound for detection by electron spin resonance spectroscopy and a suitable liquid carrier, wherein the spin label compound has a structural formula:

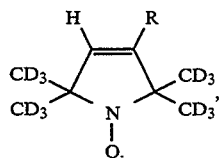

wherein R is selected from the group consisting of amido (—CO—NH$_2$); alkylcarbonyl, carbocyclic arylcarbonyl (—CO—R'); alkoxycarbonyl, aryloxycarbonyl (—CO—OR'); and substituted amido carbonyl (—CO—NHR'), wherein R' is an alkyl, substituted alkyl, carbocyclic aryl or substituted carbocyclic aryl group.

4. The composition of claim 3 capable of exhibiting a broadened electron spin resonance spectrum upon interaction with a paramagnetic species in an aqueous test sample.

5. The composition of claim 3 capable of exhibiting a broadened electron spin resonance spectrum upon interaction with a paramagnetic species in a biological test sample.

6. The composition of claim 5 wherein the biological sample is a living organism.

7. The composition of claim 3 capable of exhibiting a broadened electron spin resonance spectrum upon interaction with a paramagnetic species, wherein the paramagnetic species is molecular oxygen.

8. The composition of claim 3 capable of exhibiting a broadened electron spin resonance spectrum upon interaction with a paramagnetic species, wherein the paramagnetic species is an organic free radical.

9. The composition of claim 3 wherein the spin label compound has the structural formula:

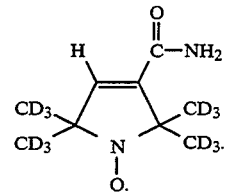

10. The composition of claim 3 wherein the suitable liquid carrier is water.

* * * * *

UNITED STATES PATENT AND TRADEMARK OFFICE
CERTIFICATE OF CORRECTION

PATENT NO. : 5,431,901  Page 1 of 2
DATED : July 11, 1995
INVENTOR(S) : Howard J. Halpern et al.

It is certified that error appears in the above-indentified patent and that said Letters Patent is hereby corrected as shown below:

Column 4, line 10, "nomalous" should be -- "Anomalous --.

Column 4, line 10, please delete " "A ".

Column 8, line 60, "shoeing" should be --showing--.

Column 9, line 31, "statues" should be --states--.

Column 10, line 39, "Deflect" should be --reflect--.

Column 14, line 13, "atoms the" should be --atoms on the--.

Column 15, line 13, "...3,5tet-..." should be --...3,5-tet...--.

Column 16, line 20, "retool" should be --mmol--.

Column 17, line 61, "df" should be --of--.

UNITED STATES PATENT AND TRADEMARK OFFICE
CERTIFICATE OF CORRECTION

PATENT NO. : 5,431,901
DATED : July 11, 1995
INVENTOR(S) : Howard J. Halpern et al.

It is certified that error appears in the above-indentified patent and that said Letters Patent is hereby corrected as shown below:

Column 18, line 48, "spectrum-of" should be --spectrum of--.

Column 22, line 49, "for-the" should be --for the --.

Column 25, line 59, "With" should be --with--.

Signed and Sealed this

Twenty-sixth Day of December, 1995

Attest:

BRUCE LEHMAN

Attesting Officer

Commissioner of Patents and Trademarks